US009496099B2

(12) United States Patent
McMahon et al.

(10) Patent No.: US 9,496,099 B2
(45) Date of Patent: Nov. 15, 2016

(54) APPARATUS FOR MICROSCOPIC DETECTION OF HARDNESS

(75) Inventors: Stephen M. McMahon, Quincy, MA (US);
(Continued)

(73) Assignee: ILLINOIS TOOL WORKS INC., Glenview, IL (US)

( * ) Notice: Subject to any disclaimer, the term of this patent is extended or adjusted under 35 U.S.C. 154(b) by 52 days.

(21) Appl. No.: 14/241,875

(22) PCT Filed: Sep. 5, 2012

(86) PCT No.: PCT/US2012/053750
§ 371 (c)(1),
(2), (4) Date: Feb. 27, 2014

(87) PCT Pub. No.: WO2013/036511
PCT Pub. Date: Mar. 14, 2013

(65) Prior Publication Data
US 2014/0218793 A1 Aug. 7, 2014

Related U.S. Application Data

(60) Provisional application No. 61/531,333, filed on Sep. 6, 2011.

(51) Int. Cl.
*G02B 21/26* (2006.01)
*H01H 3/16* (2006.01)
(Continued)

(52) U.S. Cl.
CPC .................. *H01H 3/16* (2013.01); *G01N 3/42* (2013.01); *G01N 35/10* (2013.01); *G02B 7/003* (2013.01); *G02B 21/06* (2013.01); *G02B 21/26* (2013.01)

(58) Field of Classification Search
CPC ............ G01N 3/42; G01N 35/10; G02B 7/00; G02B 21/18; G02B 21/26
(Continued)

(56) References Cited

U.S. PATENT DOCUMENTS 2,713,259 A * 7/1955 Grodzinski .............. G01N 3/42
73/81
3,642,353 A 2/1972 Field
(Continued)

FOREIGN PATENT DOCUMENTS

CN 2188762 2/1995
CN 2669176 1/2005
(Continued)

OTHER PUBLICATIONS

Kehlet, "Angularly Adjustable Lens Holder", DK63545C, May 1945, translation.*
ISR for PCT/US2012/053750 mailed Dec. 17, 2013.

*Primary Examiner* — Bumsuk Won
*Assistant Examiner* — Wen Huang
(74) *Attorney, Agent, or Firm* — McCarter & English, LLP

(57) ABSTRACT

An adjustable stage mount includes a housing having a base defining a hole and an adjustable stage including a ball joint extension that rotatably engages the hole and is rotatably securable about the x-, y-, and z-axes. An adjustable indenter mount includes a housing defining a hole and an adjustable indenter including a ball joint extension that rotatably engages the hole and is rotatably securable about the x-, y-, and z-axes. A collision protection switch includes a first plate having three pairs of electrically conductive spaced apart pins wired to a voltage source in an open circuit, and a second plate having three electrically conductive balls. A spring pulls the first and second plates together causing the three balls to complete the circuit. A sufficient force against the second plate causes a ball to disengage and open the circuit. A two-objective microscope includes two parallel objectives, upper and lower light sources, three half-mirrors,
(Continued)

and a camera. The camera and the half-mirrors are configured such that the camera views through either objective depending on which light source is on.

26 Claims, 19 Drawing Sheets

(75) Inventors: Rudolf M. Mayer, Neuhausen (DE); John Hitchcock, Boston, MA (US); Fritz Mueller, Munich (DE); Devin S. Dix, Boston, MA (US)

(51) Int. Cl.
  *G01N 3/42*  (2006.01)
  *G02B 7/00*  (2006.01)
  *G01N 35/10* (2006.01)
  *G02B 21/06* (2006.01)

(58) Field of Classification Search
  USPC .............. 359/384, 385, 391–394, 819, 822, 359/829–831, 871, 874–876
  See application file for complete search history.

(56) References Cited

U.S. PATENT DOCUMENTS

| 4,088,396 | A |   | 5/1978  | Edelstein |
| 5,694,257 | A | * | 12/1997 | Arnone ............... G02B 7/1805 359/822 |
| 6,239,395 | B1 |   | 5/2001  | Rosen |
| 8,857,779 | B2 | * | 10/2014 | Hornqvist ............... G01J 3/02 248/181.1 |
| 2004/0240049 | A1 |   | 12/2004 | Krueger |
| 2005/0163458 | A1 |   | 7/2005  | Nunnally et al. |
| 2010/0073793 | A1 |   | 3/2010  | Meyer et al. |

FOREIGN PATENT DOCUMENTS

| DE | 102009019256 |   | 11/2010 |
| DK | 63545 C | * | 5/1945 |
| EP | 1093144 |   | 4/2001 |
| SE | WO 2010114466 A1 | * | 10/2010 ............... G01J 3/02 |
| WO | 03034097 |   | 4/2003 |

\* cited by examiner

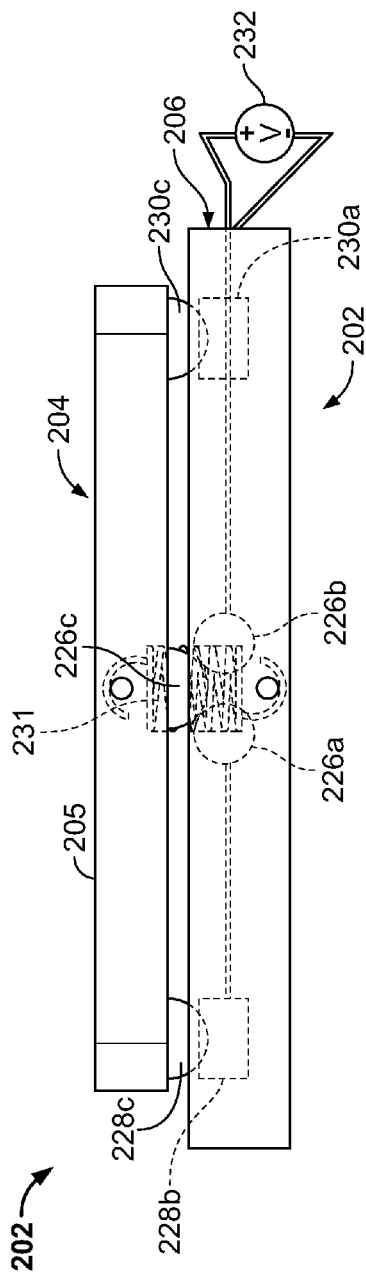
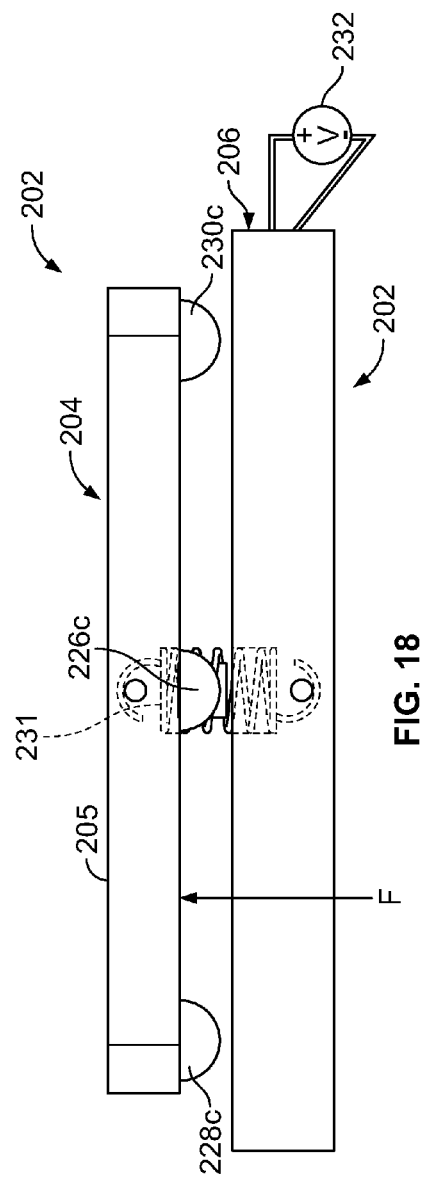
FIG. 17
FIG. 18

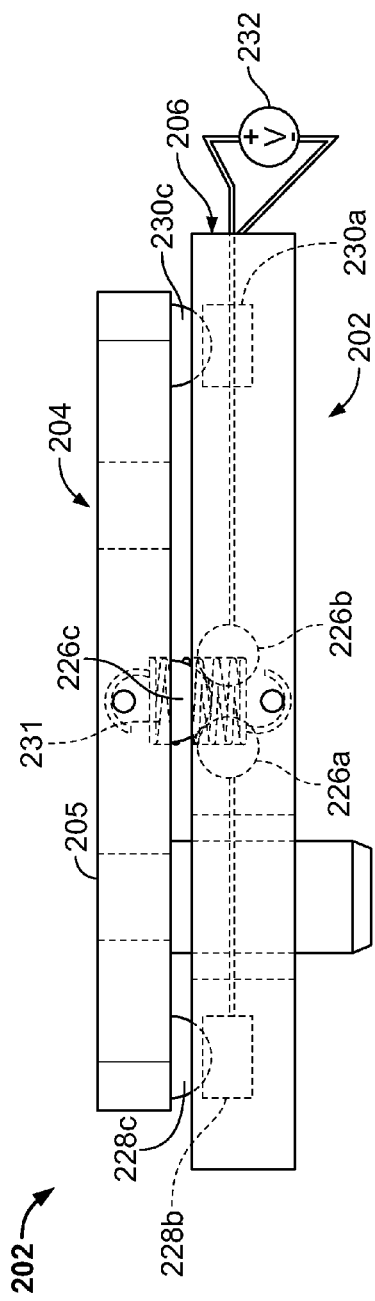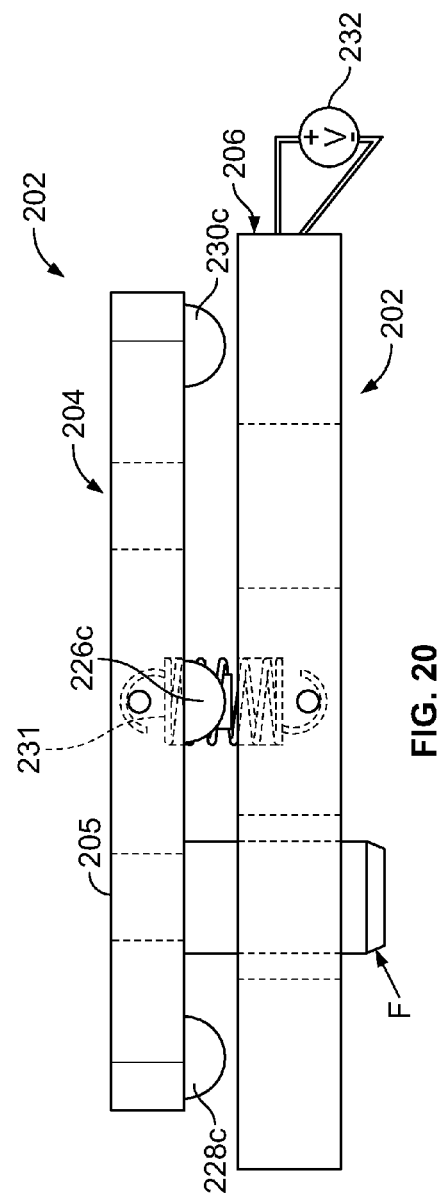

APPARATUS FOR MICROSCOPIC DETECTION OF HARDNESS

This application is a U.S. National Phase of International Patent Application No. PCT/US2012/053750 filed Sep. 5, 2012 and claims priority under 35 U.S.C. §119(e) of U.S. provisional patent application Ser. No. 61/531,333 filed on Sep. 6, 2011, the contents of which is hereby incorporated by reference in their entirety and made a part hereof.

BACKGROUND OF THE DISCLOSURE

1. Field of the Disclosure

The present disclosure relates to improvements in apparatus for microscopic detection of hardness and related apparatus.

2. Description of the Prior Art

In the prior art, hardness, the resistance of a material to permanent deformation, is typically measured on a Brinell, Rockwell or Vickers hardness testing machine. In a Vickers test, a four-sided pyramidal diamond indenter is pressed into the surface of the test sample with a controlled force. The indenter or the microscope is moved so the indent can be viewed and the lengths of the two diagonals of the indentation in the surface of the test sample are measured. The Vickers hardness of the test sample is calculated, typically by software, using the test force and the area of indentation. In Vickers testing, the indenter is typically a symmetrical four-sided pyramid which produces a square-shaped indentation. In Knoop testing, similar testing equipment is used, but a highly asymmetrical indenter is used, wherein the resulting indent is highly elongated (typically with 7:1 ratio of length to width) and the calculation of hardness is performed based on the measurement of the long diagonal.

Vickers testers may be equipped with multiple indenters (which may include both Vickers and Knoop indenters) and multiple microscope objectives all mounted on a multiple position rotatable turret. The user rotates the turret so as to position the selected indenter above the test sample, the indentation is made and the user rotates the turret so as to position a microscope objective so that the user can view and measure the indentation.

To make symmetrical indentations on a test sample, the diamond indenter must contact the surface with a precise angular orientation. Typically, the indenter axis and the surface of the test sample must be perpendicular in both axes within three arc minutes. Two adjustable horizontal axes are required because such a tight angular tolerance is typically not achievable with fixed parts, even with the most precise machining.

Wilson Tukon 2100 and Tukon 2500 testers use an arrangement of thin shims (0.001" & 0.003" thick sheet metal washers) to adjust the angle of the XY stage. Two Knoop indents (one horizontal and one vertical) are made with the unshimmed tester, indent asymmetry is measured and the measurements are used to calculate the thicknesses of the shims needed to correct the asymmetry. The shims are placed around the four bolts that clamp the XY stage to the loadframe. Finally, two more Knoop indents are made to verify the results of shimming. The Wilson Tukon testers use a coarse, uncontrolled stage rotation adjustment.

Moreover, a third indent orientation, rotation of the indent about the viewing axis must also be controlled. Opposite indent corners need to be oriented left-to-right and front-to-back within approximately a half degree. This third indent orientation is generally utilized, because indent length is measured automatically by two pairs of software filars (one pair is exactly vertical and one pair is exactly horizontal), and many users would assume that an indent with a visually perceptible tip angle would be inaccurately measured by the software filars—even though an indent with a very obvious 2.5 degree angle would actually be measured accurately (within 0.1 percent) by the filars.

Manufacturers which may adjust their indenter symmetry include Emco. Co., Qness Co., Futuretec, Newage, and Mitutoyo, possibly among others.

A fourth orientation, the rotation of the stage about the viewing axis must also be tightly controlled. As the stage traverses from left to right or front to back, any sample point must travel exactly horizontally or vertically respectively along the monitor screen.

Occasionally, the XY stage must be removed and/or reassembled to the tester frame (e.g.; when the tester is received by the customer and when servicing the tester). With the prior art stage attachment, the heavy stage must be lifted straight up off the large coarse attachment thread. It is not uncommon for the stage, as it is lifted up for removal from the tester to catch on a holding stud, causing the user to lift the stage with a jerk into the indenter above.

Additionally, a four-axis alignment device, having two translations and two rotations, exists for adjusting the alignment of tensile test specimens. This device is manufactured to the Interlaken Company and may be related to U.S. Pat. No. 5,377,549 entitled "Alignment Device and Method of Aligning", issued on Jan. 3, 1995 to Werner.

Prior art Vickers testers typically use a motorized turret to position microscope objectives and indenters. However, prior art microscopes often involve moving parts, e.g., bearings and position detent mechanisms. Sometimes, the prior art detent mechanism flexure was prone to fracture and the detent ball could wear a deep groove in the brass track, causing the detent-feel to be lost.

Wilson Tukon 2100 and Tukon 2500 testers use a five-position rotating turret that can hold any combination of microscope objectives and loadcell/indenter assemblies. One position is fixed ("home" position) and the other four positions can be made parcentric to the home position with a series of adjusting bolts.

Emco Co., Qness Co. Futuretec, Newage, and Mitutoyo among others are believed to use a rotating turret to hold and position the objectives and indenters.

OBJECTS AND SUMMARY OF THE DISCLOSURE

It is therefore an object of the present disclosure to provide an adjustable stage mount that permits a fine rotational adjustment of the stage. It is a further object of the present disclosure to provide an adjustable indenter mount that permits fine adjustments of the indenter about the x-axis, the y-axis, and the z-axis. It is still a further object of the present disclosure to provide a collision protection switch for a microscope that provides adequate notice to a user when an objective collides with a specimen, protecting the microscope from damage caused by the collision, and returns the objectives to the exact same previous position. It is yet a further object of the present disclosure to provide a two-objective microscope that requires minimal moving parts.

In one aspect, an adjustable stage mount is disclosed that includes a housing having a base defining a hole and an annular protrusion extending from the base, an adjustable stage including a mounting surface and a ball joint extension extending from the mounting surface. The ball joint extension is defined by a wall including at least one radial bore extending therethrough, and a semi-spherical end. The annular protrusion includes a plurality of xy-axis bores extending therethrough and a z-axis locking assembly that includes a pin hole and two z-axis bores. A pin is configured to engage the at least one radial bore, and a plurality of xy-axis bolts are configured to engage the plurality of xy-axis bores and to contact the ball joint extension wall. A plurality of z-axis bolts are configured to engage the two z-axis bores and to contact the pin. The semi-spherical end of the ball joint extension is configured to rotatably engage the hole.

In another aspect, an adjustable indenter mount is disclosed that includes a housing having a shoulder defining a hole and an annular protrusion, an adjustable indenter holder including an indenter tip mount and a ball joint extension extending from the indenter tip mount. The ball joint extension is defined by a wall including at least one radial bore extending therethrough, and a semi-spherical end. The annular protrusion includes a plurality of xy-axis bores extending therethrough and a z-axis locking assembly that includes a pin hole and two z-axis bores. A pin is configured to engage at least one radial bore, and a plurality of xy-axis bolts are configured to engage the plurality of xy-axis bores and to contact the ball joint extension wall. A plurality of z-axis bolts are configured to engage the two z-axis bores and to contact the pin. The semi-spherical end of the ball joint extension is configured to rotatably engage the hole.

In another aspect, a collision protection switch is disclosed that includes a first plate, a voltage source, and a second plate. The first plate is formed of an electrically insulative material and includes a first, a second, and a third pair of electrically conductive pins. The first pair, the second pair, and the third pair of electrically conductive pins each including a first pin and a second pin that are parallel and spaced apart from each other. The second plate is formed of an electrically insulative material and includes three electrically conductive spherical balls extending from a wall. The voltage source, and the first pair, the second pair, and the third pair of electrically conductive pins are wired as a series circuit such that the gap between each pin of each pair of pins creates a break in the circuit. The three electrically conductive spherical balls are configured to contact the first pair, the second pair, and the third pair of electrically conductive pins to close the circuit.

In another aspect, a two-objective microscope is disclosed that includes a first objective parallel with a second objective, an upper light source configured to provide light to the first objective, a lower light source configured to provide light to the second objective, a first half-mirror, a second half-mirror, and a camera configured to view the first objective and the second objective. The camera is configured to view the first objective when the upper light source is switched on and the second objective when the lower light source is switched on.

BRIEF DESCRIPTION OF THE DRAWINGS

Further objects and advantages of the disclosure will become apparent from the following description and from the accompanying drawings, wherein:

FIG. 17 is a side view of the collision protection switch of FIG. 15 in a closed position;

FIG. 18 is a side view of the collision protection switch of FIG. 15 in an open "collided" position;

FIG. 19 is a side view of the collision protection switch of FIG. 15 attached with a microscope objective and in a closed position;

FIG. 20 is a side view of the collision protection switch of FIG. 15 attached with a microscope objective and in an open "collided" position;

DETAILED DESCRIPTION OF THE PREFERRED EMBODIMENTS

Figure 1:
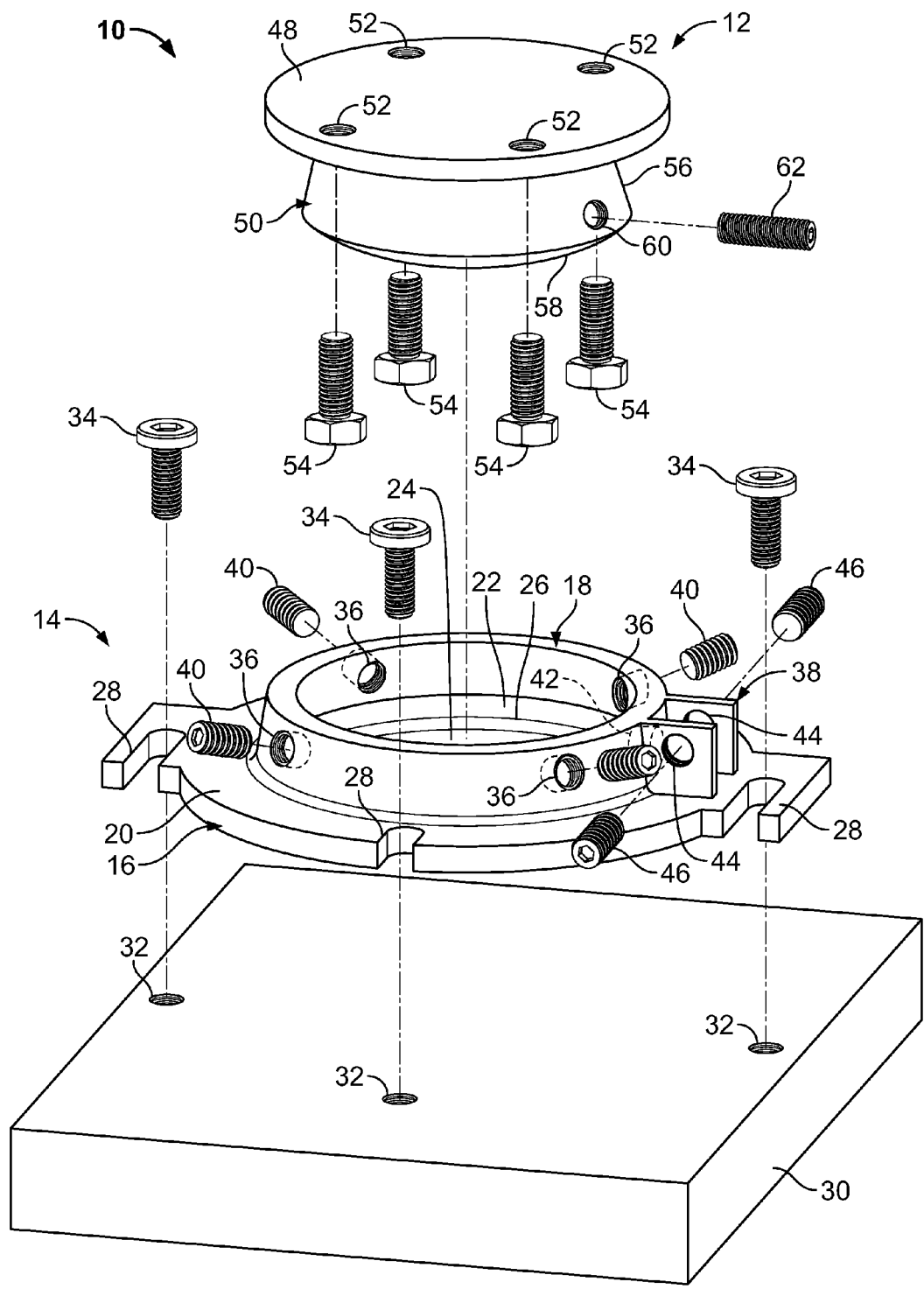
FIG. 1 is an exploded perspective view of an adjustable stage mount of the present invention.

Referring now to the drawings in detail wherein like numerals indicate like elements throughout the several views, implemented.

FIGS. 1-6 show a first aspect of an adjustable stage mount 10 of the present invention. FIG. 1 is an exploded perspective view of the adjustable stage mount 10 of the present invention. The adjustable stage mount 10 includes an adjustable stage 12 and a housing 14. The housing 14 includes a base 16 and an annular protrusion 18 extending upwardly from a top surface of the base 16, such that the base 16 is divided in to an exterior flange 20 and an interior flange 22. The base 16 is generally a disc-shaped member having a circular hole 24 with rounded edges 26 through the center that acts as a "socket." However, one of ordinary skill in the art would understand that the base 16 could be of any geometry and include a perimeter that is not limited to circular, but may be square, rectangular, triangular, etc. The exterior flange 20 includes a plurality of mounting slots 28 formed therein. The plurality of mounting slots 28 allow for the base 16 to be mounted to a machine mounting plate 30. The machine mounting plate 30 includes a plurality of threaded holes 32 with matching bolts 34 for securing the base 16 in position. The shaft of each one of the bolts 34 fits within one of the plurality of mounting slots 28 of the base 16 and can be tightened to secure the base 16 to the machine mounting plate 30.

Figure 2:
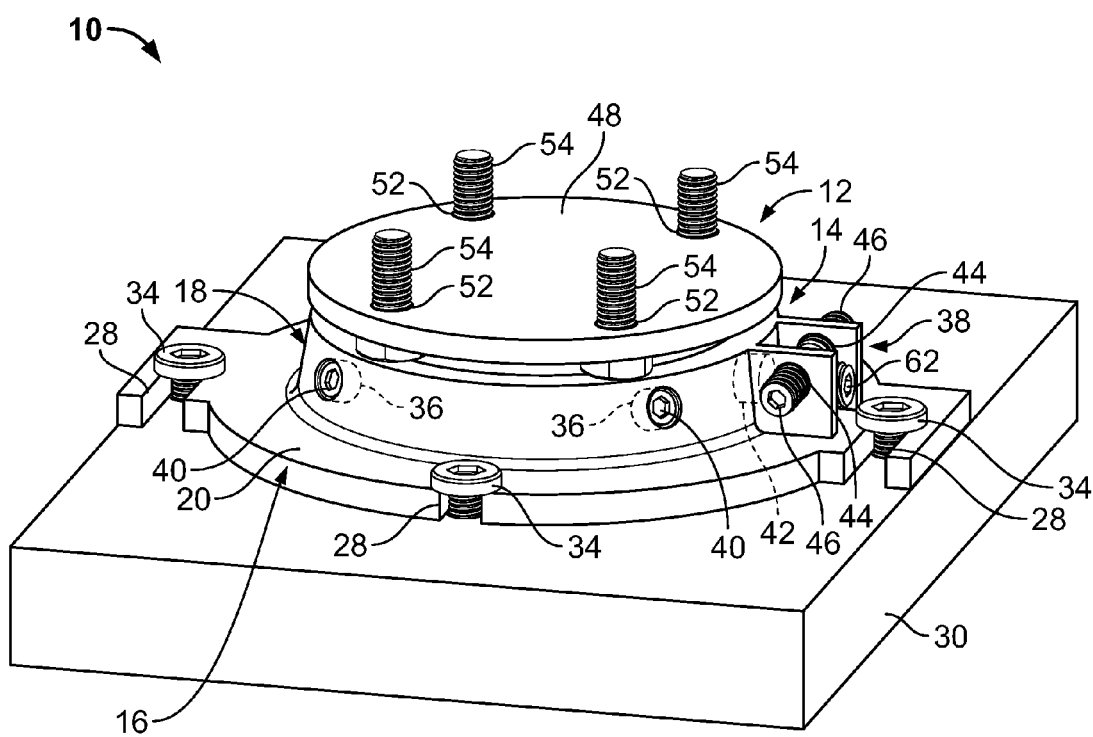
FIG. 2 is a perspective view of the adjustable stage mount of FIG. 1 assembled.
Figure 3:
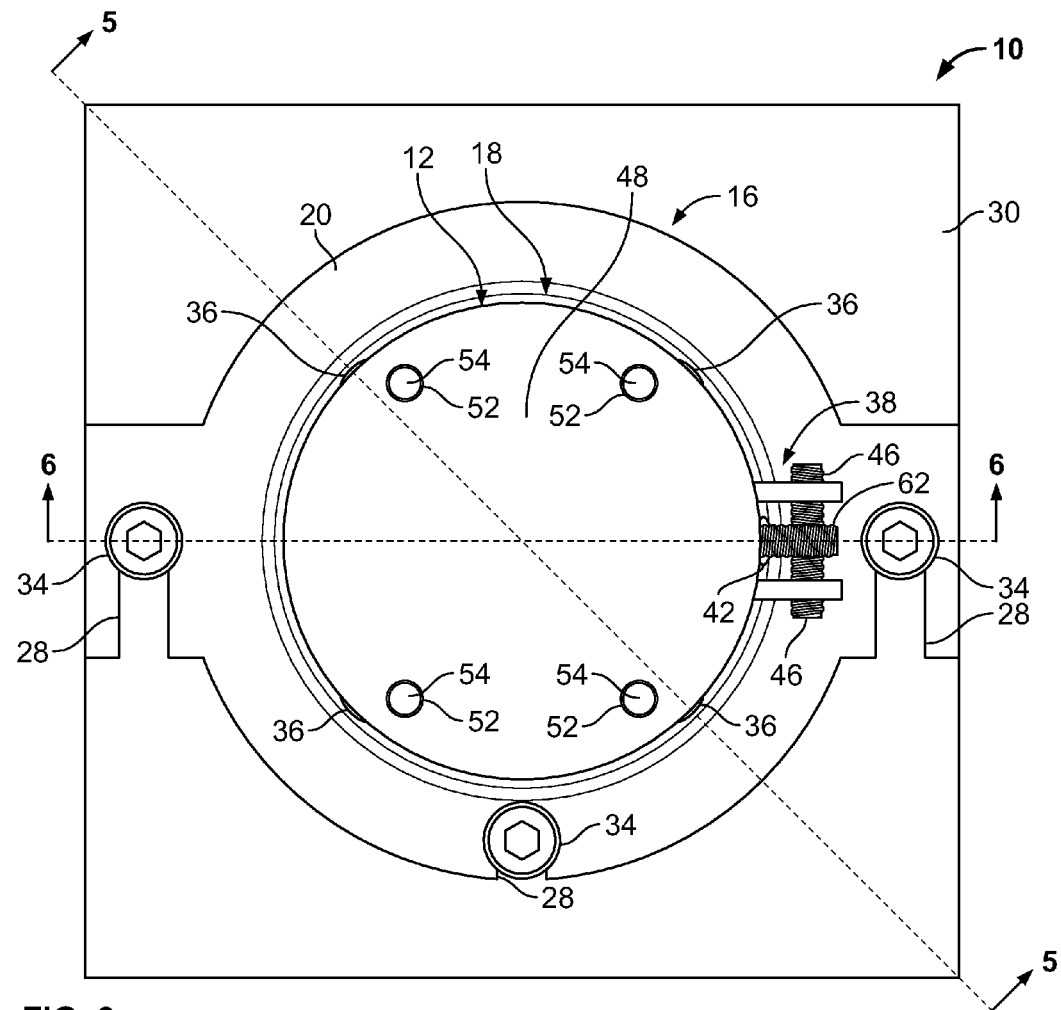
FIG. 3 is a top view of the assembled adjustable stage mount of FIG. 2.
Figure 4:
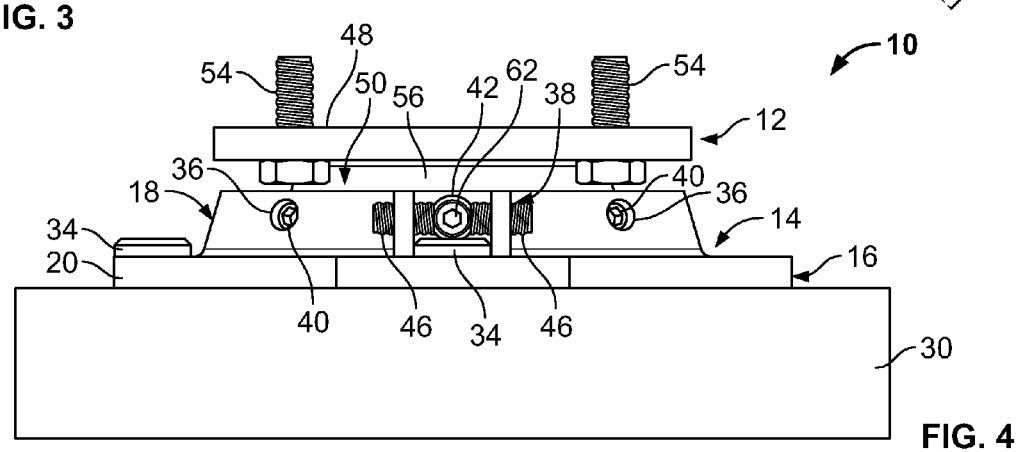
FIG. 4 is a right side elevational view of the assembled adjustable stage mount of FIG. 2.

As shown in FIGS. 1-3, the annular protrusion 18 includes four threaded xy-axis set bores 36 extending there through and a z-axis locking apparatus 38. The xy-axis set bores 36 are radial, generally configured on a downward slope, and include four matching xy-axis set bolts 40, which will be discussed in greater detail below. The z-axis locking apparatus 38 includes a radial pin hole 42 that extends through the width of the annular protrusion 18, two z-axis set bores 44, and two z-axis set bolts 46. The z-axis set bores 44 are positioned on opposite sides of the radial pin hole 42 such that they are across from each other and radial with respect to the radial pin hole 42. The z-axis set bolts 46 are provided to match the z-axis set bores 44, which will be discussed in greater detail below.

Figure 5:
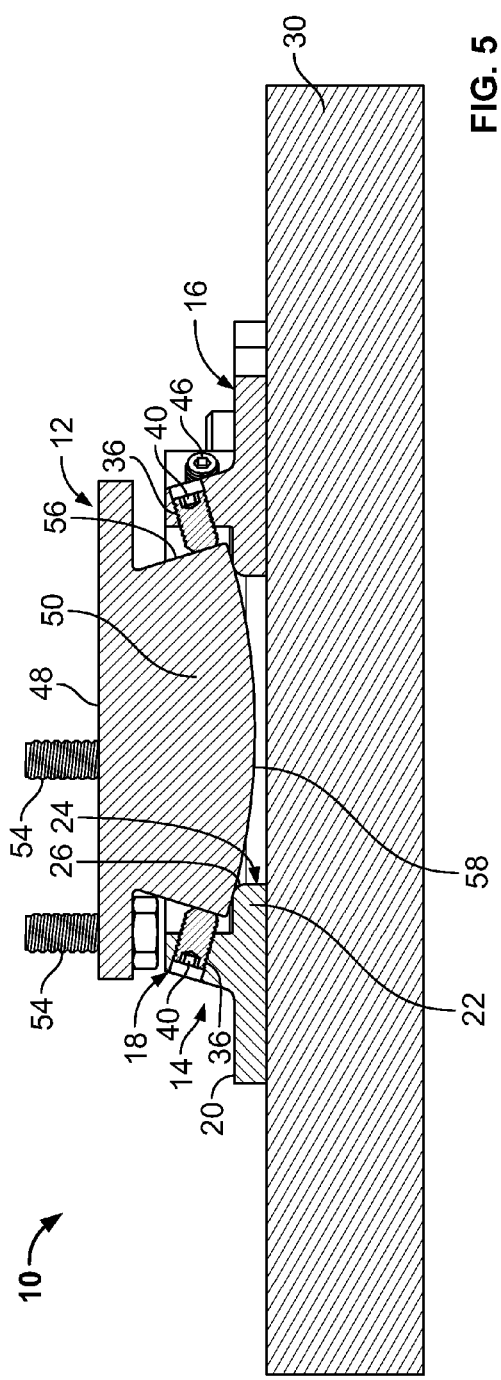
FIG. 5 is a cross-section of the assembled adjustable stage mount of FIG. 2 along line 5-5 of FIG. 3.
Figure 6:
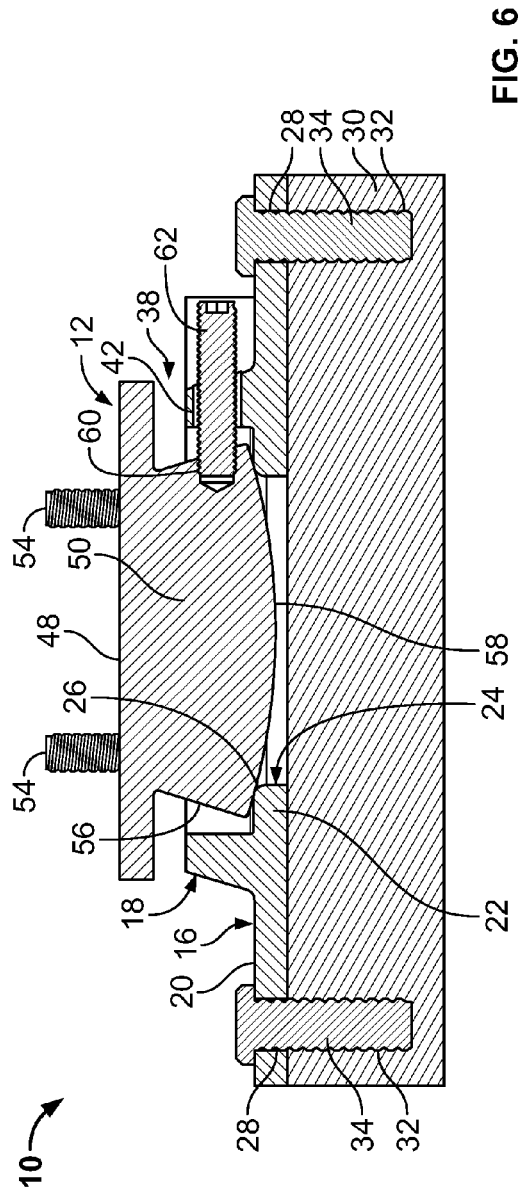
FIG. 6 is a cross-section of the assembled adjustable stage mount of FIG. 2 along line 6-6 of FIG. 3.

The adjustable stage 12 includes a mounting plate 48 and a semi-spherical ball joint extension 50 extending from a bottom surface of the mounting plate 48. The mounting plate 48 includes a plurality of holes 52 extending therethrough that allow a sample material mounting surface (e.g. an X-Y stage) to be secured thereto. The plurality of holes 52 may be threaded so that bolts 54 can be threadably engaged therewith, or they may simply be threadless bores. As shown in FIGS. 5 and 6, the ball joint extension 50 has a geometry that can be described as a rounded conical base. That is, the ball joint extension 50 includes a conical wall 56 extending outwardly from a bottom surface of the mounting plate 48 and ending at a semi-spherical base 58. The ball joint extension 50 also includes at least one threaded bore 60 through the conical wall 56 that is substantially perpendicular to a central axis of the ball joint extension 50. The threaded bore 60 permits a z-axis locking pin 62 to be threaded in for a permanent connection. This adjustable stage assembly 12 can be assembled into the housing 14 by tilting the adjustable stage 12, guiding the pin 62 into the hole 42. Alternatively, the radial pin hole 42 may be in the form of a notch that extends from the top of the annular protrusion 18 so that the z-axis locking pin 62 can be engaged with the threaded bore 60 prior to bringing the housing 14 and the adjustable stage 12 together without the need to tilt the adjustable stage while mounting it. Furthermore, the radial pin hole 42 has a diameter that is greater than the diameter of the z-axis locking pin 62. This is so that the adjustable stage 12 can enjoy a certain degree of freedom in regards to the x-, y-, and z-axes. More specifically, because there is a certain amount of space or "play" between the radial pin hole 42 and the z-axis locking pin 62 the adjustable stage 12 can be rotated a set amount of degrees about the x-axis, the y-axis, and the z-axis before the z-axis locking pin 62 contacts the wall of the radial pin hole 42.

Next, the user can begin to threadably engage the plurality of xy-axis set bolts 40 with the xy-axis set bores 36, and the z-axis set bolts 46 with the z-axis set bore 44. Once the xy-axis set bolts 40 and the z-axis set bolts 46 are in place, the adjustable stage 12 can be rotated about the x-, y-, and z-axes until it is in the desired position. When the adjustable stage 12 is in the desired position, the xy-axis set bolts 40 are tightened until their flattened bearing surface contacts the conical wall 56. Each of the plurality of xy-axis set bolts 40 are tightened until the adjustable stage mount 10 is secured and set in the desired position. Setting the adjustable stage mount 10 with the xy-axis set bolts 40 directly results in the adjustable stage mount 10 being set or restricted from rotation about the x-axis and y-axis. If a user desires the adjustable stage mount 10 to be rotated about either they x-axis or the y-axis all he/she needs to do is slightly loosen one xy-axis set bolt 40 restricting that rotational axis and further tighten the xy-axis set bolt 40 opposite the xy-axis set bolt 40 that was loosened. This will result in the adjustable stage mount 10 rotating about the desired axis the amount of degrees corresponding to the amount that the xy-axis set bolt 40 was loosened. This can be similarly done in the other rotational direction until the adjustable stage mount 10 is in the desired xy-position. It should be understood that each individual xy-axis set bolt 40 can be tightened or loosened by an amount different than the other xy-axis set bolts 40, e.g., each individual set bolt 40 can be manipulated individual of the other xy-axis set bolts 40. The importance of this feature is that the adjustable stage mount 10 does not have to be removed to be adjusted, and can be adjusted by very small rotational amounts in the measurement of fractions of degrees.

Once all of the xy-axis set bolts 40 are tightened, the user can tighten the z-axis set bolts 46 until their flattened bearing surface contacts the z-axis locking pin 62. Both of the z-axis set bolts 46 are tightened until the adjustable stage mount 10 is secured and set in the desired position. Setting the adjustable stage mount 10 with the z-axis set bolts 46 directly results in the adjustable stage mount 10 being set or restricted from rotation about the z-axis. If a user desires the adjustable stage mount 10 to be rotated about the z-axis all he/she needs to do is slightly loosen one z-axis set bolt 46 and further tighten the opposite z-axis set bolt 46. This will result in the adjustable stage mount 10 rotating about the z-axis the amount of degrees corresponding to the amount that the z-axis set bolt 46 was loosened. The importance of this feature is that the adjustable stage mount 10 does not have to be removed to be adjusted, and can be adjusted by very small rotational amounts in the measurement of fractions of degrees.

The adjustable stage mount 10 can be used with many different machines and particularly hardness testing machines, e.g., a Brinell, a Rockwell, a Vickers, and/or a Knoop machine/indenter. By allowing minute rotational changes in the x-, y-, and z-axes, the adjustable stage mount 10 makes it easier to make symmetrical indents on a test sample, such that an indenter contacts the surface at a precise angular orientation.

Figure 7:
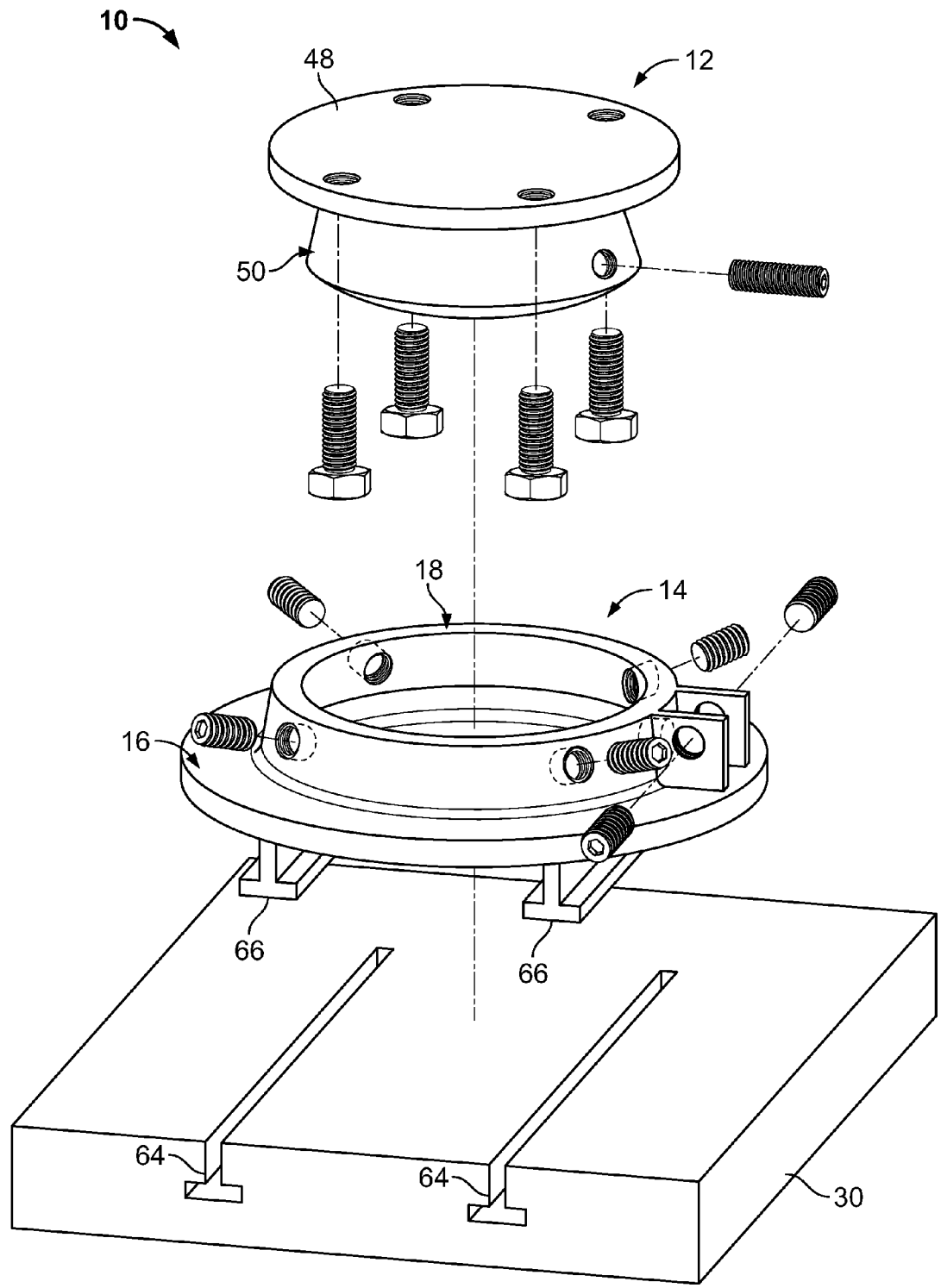
FIG. 7 is a perspective view of another embodiment of the adjustable stage mount of the present invention.
Figure 8A:
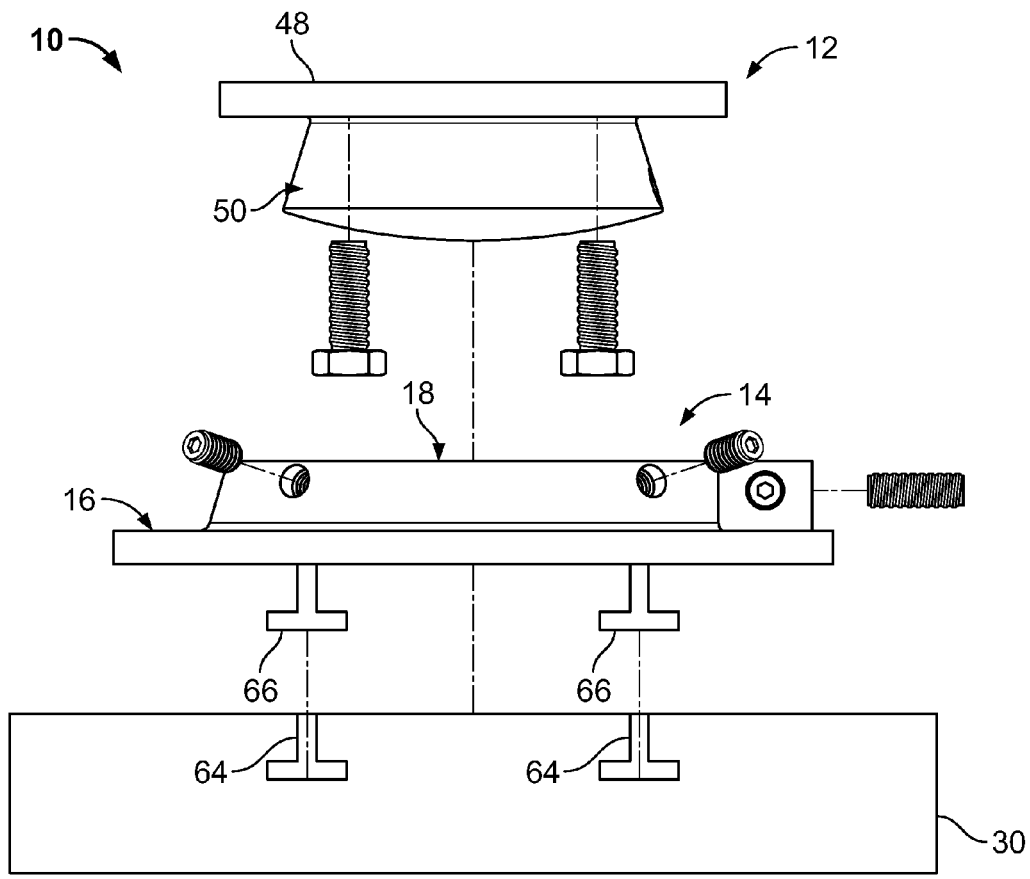
FIG. 8a is a front view of the adjustable stage mount of FIG. 7.
Figure 8B:
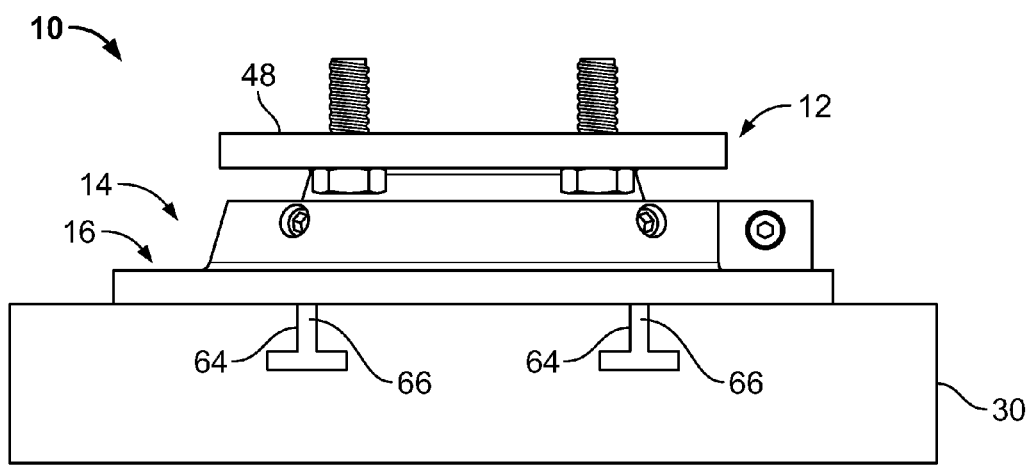
FIG. 8b is a perspective view of the adjustable stage mount of FIG. 7 assembled.

FIGS. 7-8*b* show a further embodiment of the adjustable stage mount 10 of the present invention. More specifically, FIGS. 7-8*b* shown an alternative method of mounting the adjustable stage mount 10 of the present invention to a hardness testing machine. As shown, the adjustable stage mount 10 does not include the plurality of mounting slots 28 formed in the exterior flange 20 of the embodiment of FIGS. 1-6, nor does the machine mounting plate 30 include a plurality of threaded holes 32. Instead, the machine mounting plate 30 includes two tee slots 64 while the base 16 includes two tee protrusions 66 extending from a bottom wall thereof. The two tee slots 64 and the two tee protrusions 66 are configured to be symmetrically matching such that the two tee protrusions 66 can slide in to the two tee slots 64. As such, to mount the base 16 on to the machine mounting plate 30 one would simply align the two tee protrusions 66 with the two tee slots 64 and slide the base 16 forward, locking the base 16 in position.

Figure 9:
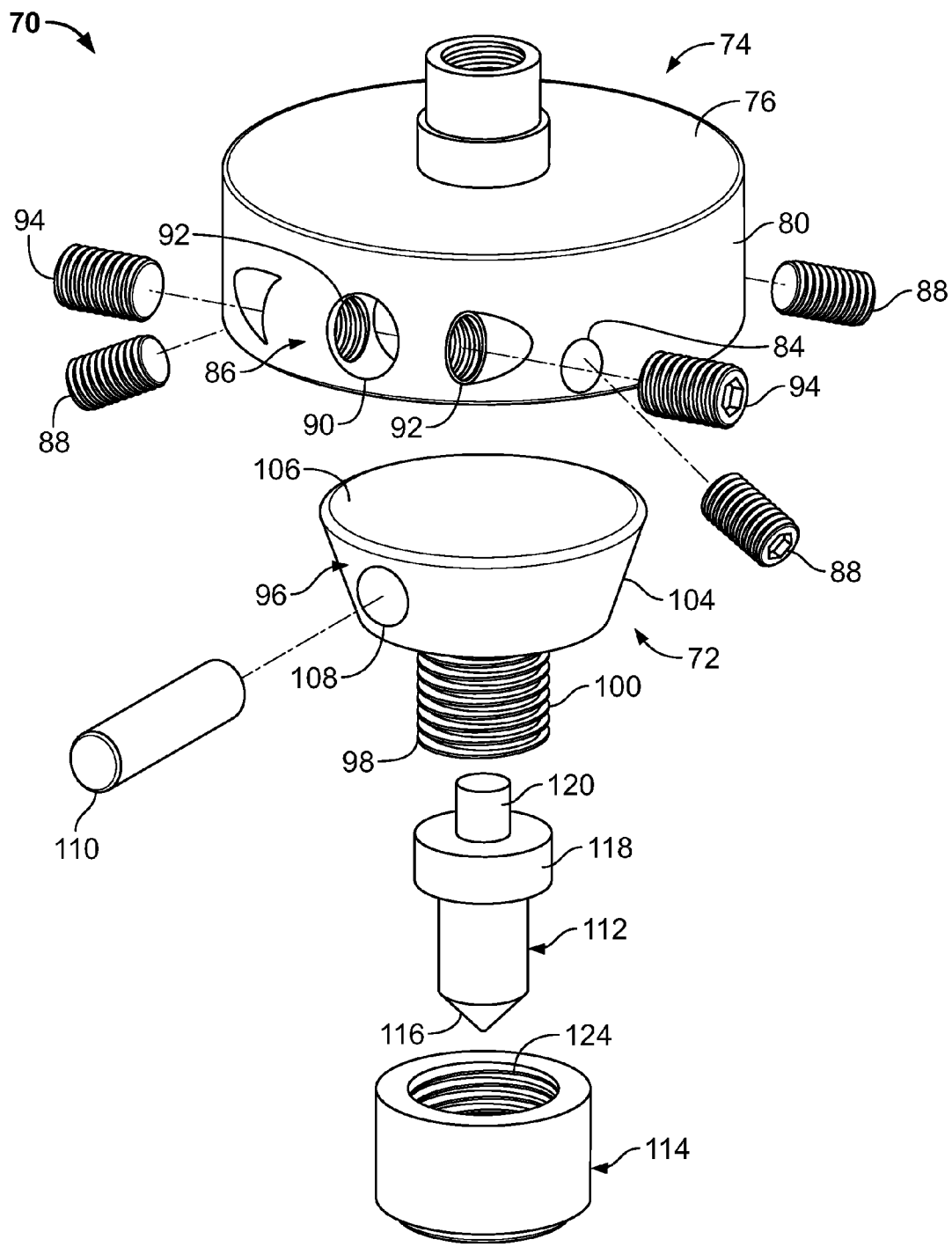
FIG. 9 is an exploded perspective view of an adjustable indenter mount of the present invention.
Figure 10:
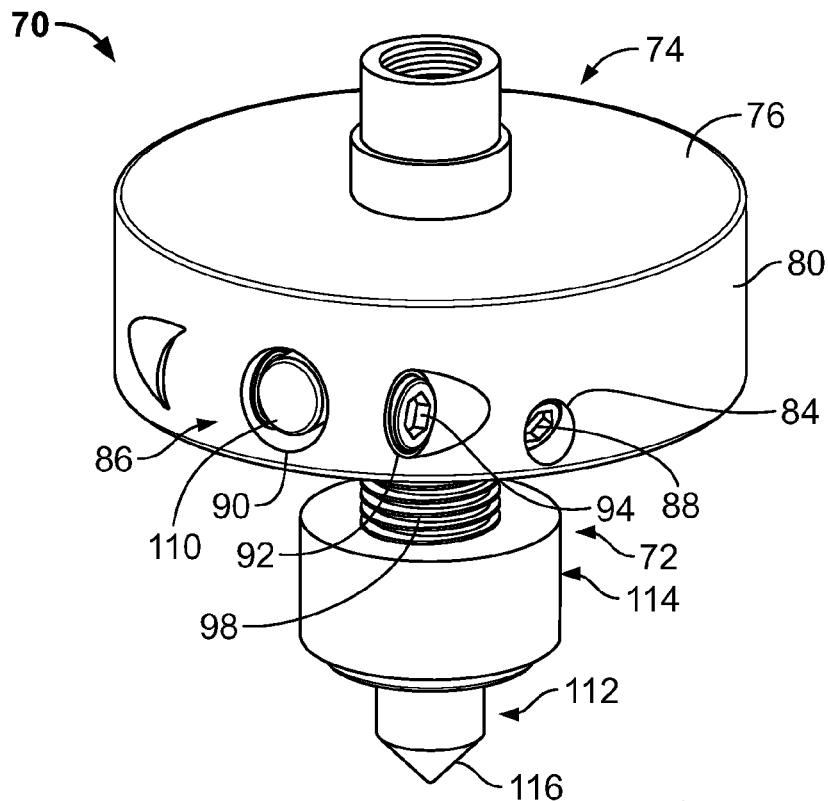
FIG. 10 is a perspective view of the adjustable indenter mount of FIG. 9 assembled.
Figure 11:
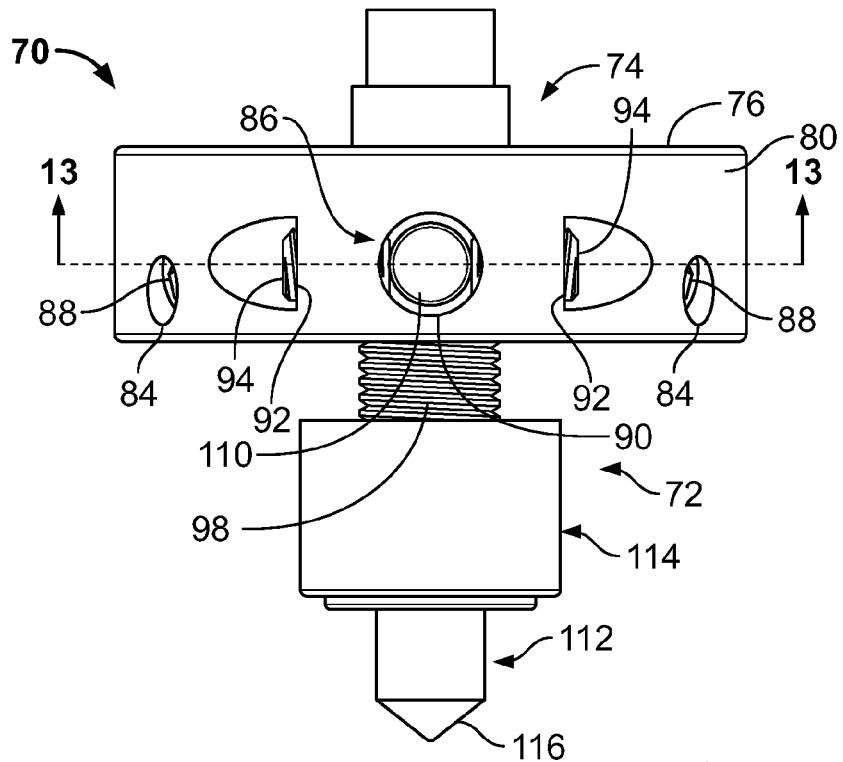
FIG. 11 is a front view of the adjustable indenter mount of FIG. 9.
Figure 12:
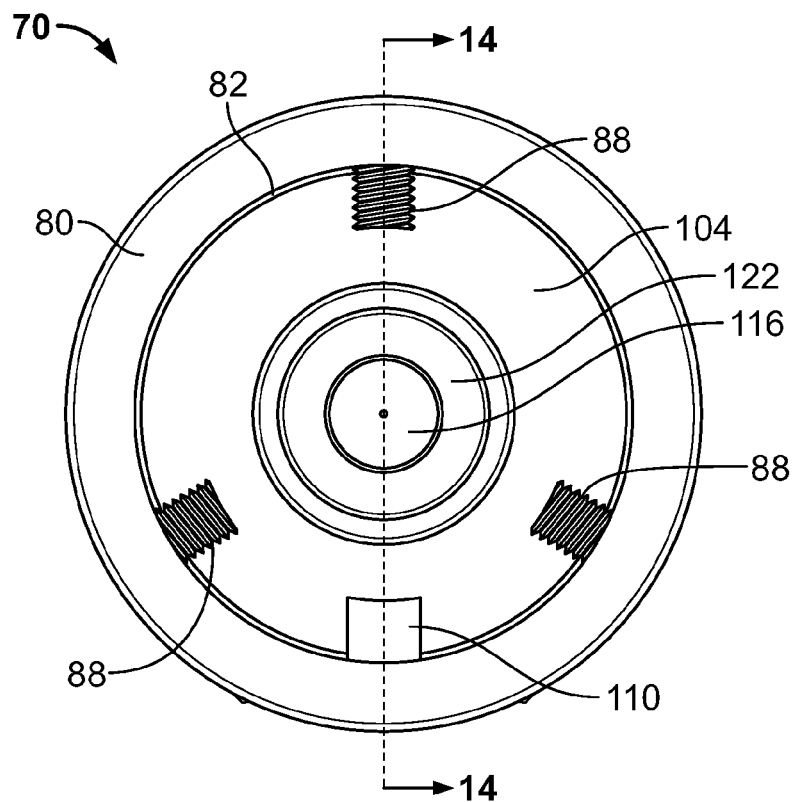
FIG. 12 is a bottom view of the adjustable indenter mount of FIG. 9.

FIGS. 9-14 show an adjustable indenter mount 70 of the present invention. FIG. 9 is an exploded perspective view of the adjustable indenter mount 70 of the present invention. As shown, the adjustable indenter mount 70 includes an adjustable indenter holder 72 and a housing 74. The housing 74 includes a base 76 and an annular protrusion 80 extending upwardly from a lower surface of the base 76. The base 76 may include a projection allowing it to be connected to a hardness testing machine. The base 76 includes a circular shoulder 82 having rounded edges and extending downwardly from a bottom surface of the base 76 that acts as a "socket."

As shown in FIGS. 9-14, the annular protrusion 80 includes three threaded xy-axis set bores 84 equidistantly spaced apart and extending there through, and a z-axis locking apparatus 86. The xy-axis set bores 84 are radial, generally configured on an upward slope, and include three matching xy-axis set bolts 88, which will be discussed in greater detail below. The z-axis locking apparatus 86 includes a radial pin hole 90 that extends through the width of the annular protrusion 80, two z-axis set bores 92, and two z-axis set bolts 94. The z-axis set bores 92 are positioned on opposite sides of the radial pin hole 90 such that they are across from each other and radial with respect to the radial pin hole 90. The z-axis set bolts 94 are provided to match the z-axis set bores 92, which will be discussed in greater detail below.

Figure 13:
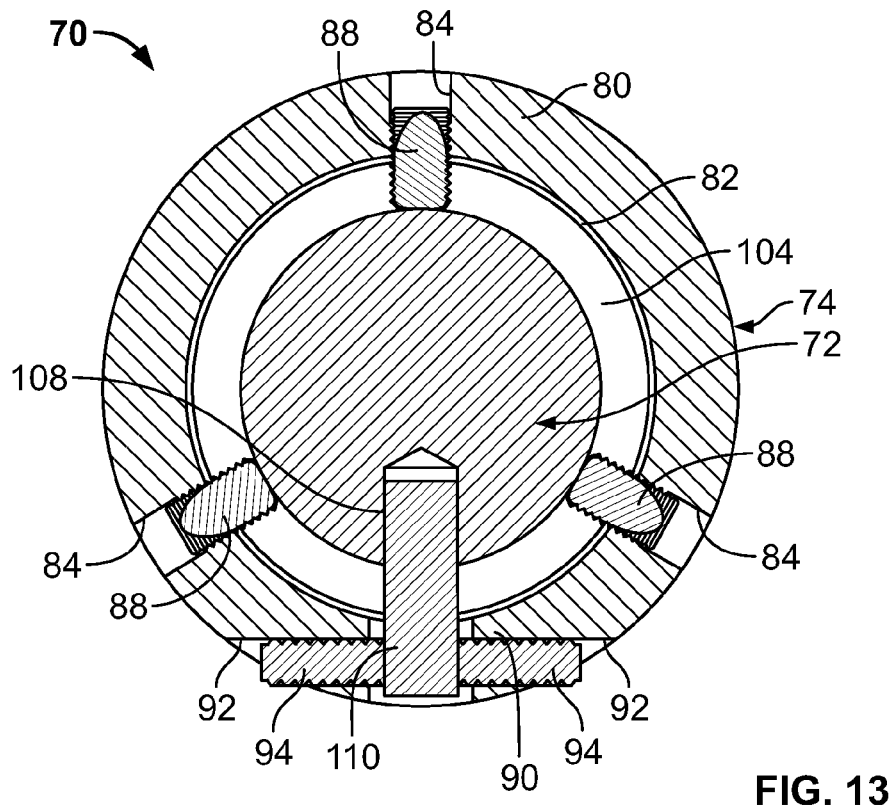
FIG. 13 is a cross-section of the assembled adjustable indenter mount of FIG. 9 along line 13-13 of FIG. 11.
Figure 14:
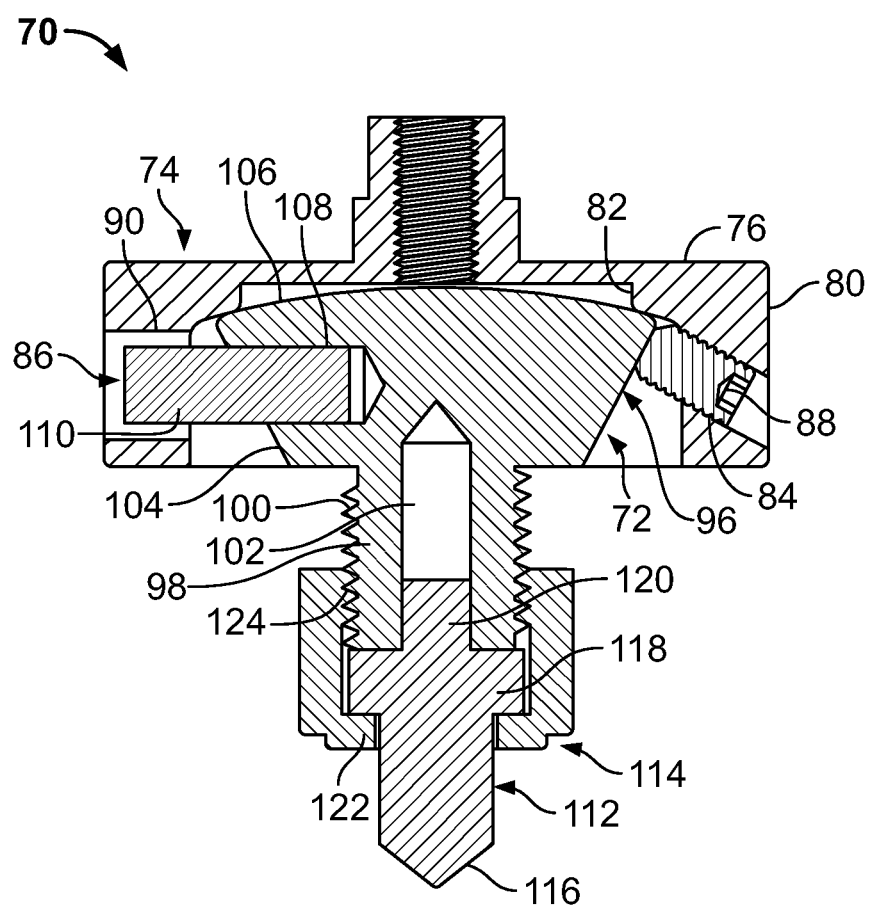
FIG. 14 is a cross-section of the assembled adjustable indenter mount of FIG. 9 along line 13-13 of FIG. 12.

The adjustable indenter 72 includes a ball joint extension 96 and a mounting boss 98 extending from a bottom surface of the ball joint extension 96. The mounting boss 98 includes external threading 100 and a central internal bore 102 that may extend through the ball joint extension 96. As shown in FIGS. 13 and 14, the ball joint extension 96 has a geometry that can be described as a rounded conical base. That is, the ball joint extension 96 includes a conical wall 104 extending outwardly from mounting boss 98 and ending at a semi-spherical base 106. The ball joint extension 96 also includes at least one bore 108 through the conical wall 104 that is substantially perpendicular to a central axis A of the ball joint extension 96. The bore 108 permits a z-axis positioning and locking pin 110 to be pressed therein.

The adjustable indenter mount 70 further includes an indenter tip 112 and a locking collar 114. The indenter tip 112 includes a specimen engagement portion 116, a collar 118, and a locating portion 120. The locating portion 120 is configured to be inserted into the central internal bore 102 of the mounting boss 98. The locking collar 114 is generally a hollow cylinder having a shoulder 122 that extends inward at one end and internal threading 124 at the opposite end. The internal threading 124 is configured to threadably engage the external threading 100 of the mounting boss 98. When the locating portion 120 is inserted into the central internal bore 102, the collar 118 abuts a face of the mounting boss 98 and the locking collar 114 can be placed over the indenter tip 112, threadably engaged with the mounting boss 98, and tightened until the shoulder 122 engages the collar 118, and the collar 118 is tightly secured forcing an upper surface of the collar 118 against the lower surface of the mounting boss 98.

During operation, a user would place the adjustable indenter 72 in to the housing 74 so that a portion of the ball joint extension 96 is positioned within the annular protrusion 80 and the semi-spherical base 106 engages the rounded edges of the circular shoulder 82. The engagement of the semi-spherical base 106 with the rounded edges of the circular shoulder 82 creates a ball and socket joint, such that three rotational degrees of freedom are present, e.g., about the x-axis, the y-axis, and the z-axis, but no translational freedom is allowed. The z-axis locking pin 110 is unthreaded and is pressed into the bore 108. This assembly can be loaded into the bore 90 in the annular protrusion 80 by tipping the adjustable indenter holder 72 and aiming the pin 110 toward the bore 108. Furthermore, the radial pin hole 90 has a diameter that is greater than the diameter of the z-axis locking pin 110. This clearance facilitates assembly and allows the adjustable indenter 72 to enjoy a certain degree of freedom in regards to the x-, y-, and z-axes. More specifically, because there is a certain amount of space or "play" between the radial pin hole 90 and the z-axis locking pin 110 the adjustable indenter 72 can be rotated a set amount of degrees about the x-axis, the y-axis, and the z-axis before the z-axis locking pin 110 contacts the wall of the radial pin hole 90.

Next, the user can begin to threadably engage the plurality of xy-axis set bolts 88 with the xy-axis set bores 84, and the z-axis set bolts 94 with the z-axis set bore 92. Once the xy-axis set bolts 88 and the z-axis set bolts 94 are in place, the adjustable indenter 72 can be rotated about the x-, y-, and z-axes until it is in the desired position. When the adjustable indenter 72 is in the desired position, the xy-axis set bolts 88 are tightened until their flattened bearing surface contacts the conical wall 104. Each of the plurality of xy-axis set bolts 88 are tightened until the adjustable indenter 72 is secured and set in the desired position. Setting the adjustable indenter 72 with the xy-axis set bolts 88 directly results in the adjustable indenter 72 being set or restricted from rotation about the x-axis and y-axis. If a user desires the adjustable indenter 72 to be rotated about either they x-axis or the y-axis all he/she needs to do is slightly loosen one xy-axis set bolt 88 restricting that rotational axis and further tighten the other xy-axis set bolts 88. This will result in the adjustable indenter 72 rotating about the desired axis the amount of degrees corresponding to the amount that the xy-axis set bolt 88 was loosened. This can be similarly done in the other rotational direction until the adjustable indenter 72 is in the desired xy-position. For example, one could slightly loosen two of the xy-axis set bolts 88 and tighten the third xy-axis set bolt 88 to rotate the adjustable indenter 72 in that radial direction. It should be understood that each individual xy-axis set bolt 88 can be tightened or loosened by an amount different than the other xy-axis set bolts 88, e.g., each individual set bolt 88 can be manipulated individual of the other xy-axis set bolts 88. The importance of this feature is that the adjustable indenter 72 does not have to be removed to be adjusted, and can be adjusted by very small rotational amounts in the measurement of fractions of degrees. The center of the semi-spherical base 106 may also be located at the tip of the indenter 11, such that the x & y position of the indenter tip does not change as the indent symmetry is adjusted. This makes it easy to view and compare the results of the symmetry adjustments made.

Once all of the xy-axis set bolts 88 are tightened, the user can tighten the z-axis set bolts 94 until their flattened bearing surface contacts the z-axis locking pin 110. Both of the z-axis set bolts 94 are tightened until the adjustable indenter 72 is secured and set in the desired position. Setting the adjustable indenter 72 with the z-axis set bolts 94 directly results in the adjustable indenter 72 being set or restricted from rotation about the z-axis. If a user desires the adjustable indenter 72 to be rotated about the z-axis all he/she needs to do is slightly loosen one z-axis set bolt 94 and further tighten the opposite z-axis set bolt 94. This will result in the adjustable indenter 72 rotating about the z-axis the amount of degrees corresponding to the amount that the z-axis set bolt 94 was loosened.

The adjustable indenter 72 can be used with, a Vickers, and/or a Knoop machine/indenter. By allowing minute rotational changes in the x-, y-, and z-axes, the adjustable indenter 72 makes it easier and quicker to make symmetrical indents on a test sample, such that an indenter contacts the surface at a precise angular orientation. Furthermore, because the adjustment is done at the indenter, the stage stays in place during adjustment and the focus plane is unaffected by adjustments.

Figure 15:
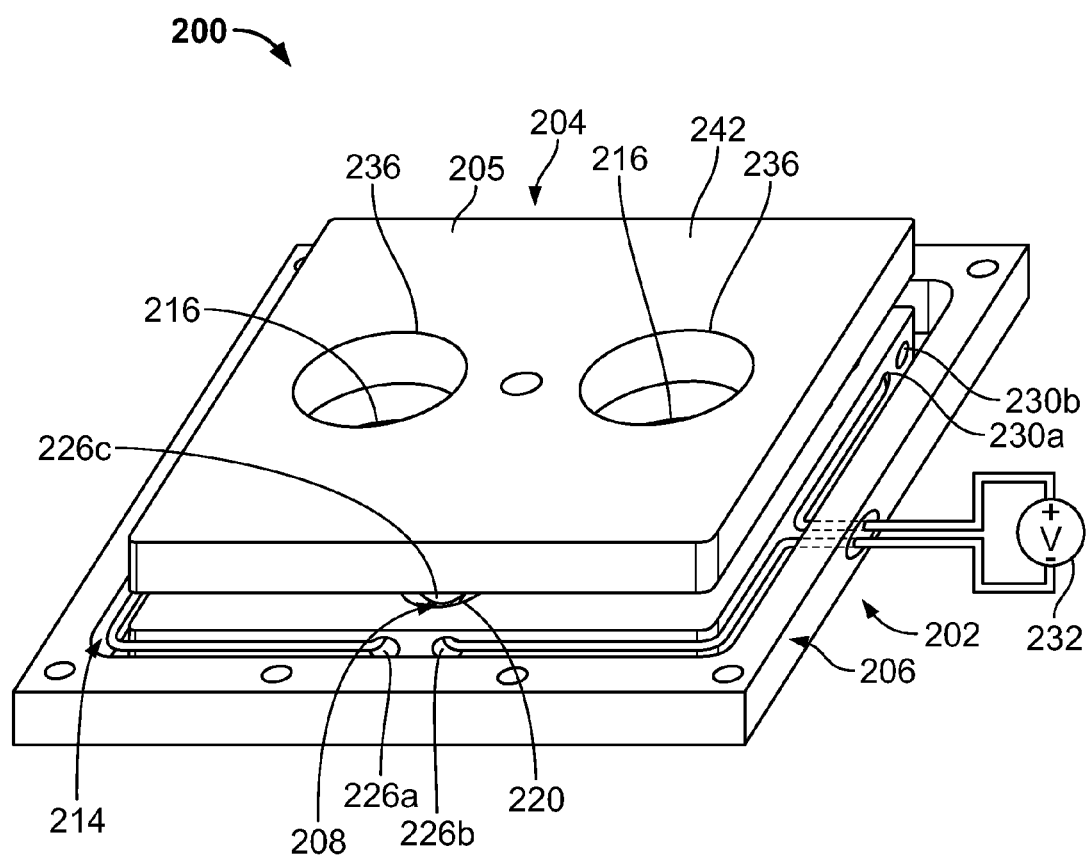
FIG. 15 is a perspective view of a collision protection switch of the present invention.

FIGS. 15-21b illustrate a collision protection switch 200 of the present invention. As shown in FIG. 15, the collision protection switch 200 includes a first plate 202 and a second plate 204. As shown in FIG. 16a, the first plate 202 includes a housing 206 formed of an electrically insulative material, e.g., plastic or hard anodized aluminum, three pin chambers 208, 210, 212, one or more circuit channels 214, two objective holes 216, and a spring hole 228. The three pin pockets 208, 210, 212 are formed within the housing 206 with a circular bore 220, 222, 224 extending from a top surface of the housing 206 in to each of the pin pockets 208, 210, 212. Each circular bore 220, 222, 224 provides access to the interior of a respective one of the pin pockets 208, 210, 212. Each pin pocket 208, 210, 212 includes a pair of parallel pins 226, 228, 230 secured therein and formed of an electrically conductive material. Importantly, each first pin 226a, 228a, 230a of each respective pair of parallel pins 226, 228, 230 is spaced apart from the opposite or second pin 226b, 228b, 230b such that they are not in contact with each other, the importance of this aspect will be discussed below.

The one or more circuit channels 214 are configured to allow the pins 226a, 228a, 230a, 226b, 228b, 230b to be wired together in a "broken" series circuit. That is, the first pin 226a of the first pair of parallel pins 226 is wired with the second pin 228b of the second pair of parallel pins 228 along a circuit channel 214 so as to place them in electrical communication. Similarly, the first pin 228a of the second pair of parallel pins 228 is wired with the second pin 230b of the third pair of parallel pins 230 along a circuit channel 214 so as to place them in electrical communication. Further, a voltage source 232 is wired to the second pin 226b of the first pair of parallel pins 226 and the first pin 230a of the third pair of parallel pins 230 along a circuit channel 214. Thus, the second pin 226b of the first pair of parallel pins 226 and the first pin 230a of the third pair of parallel pins 230 are in communication with the voltage source 232, but the other remaining pins 226a, 228a, 228b, 230b are not. This creates the "broken" series circuit that includes each pair of parallel pins 226, 228, 230. The importance of this aspect will be discussed in greater detail below. As discussed previously, the housing 206 is formed of an electrically insulative material so that the other remaining pins 226a, 228a, 228b, 230b are not electrified.

Figure 16A:
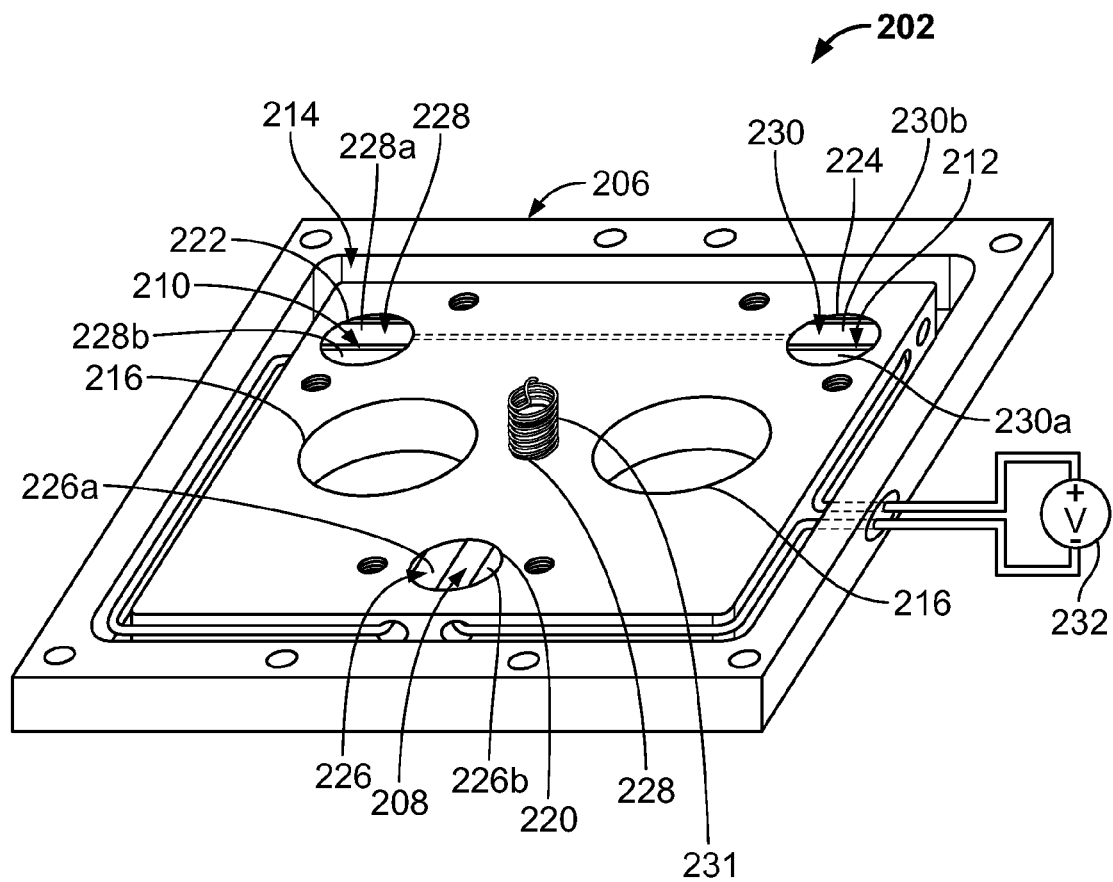
FIG. 16a is a top perspective view of a second plate of the collision protection switch of FIG. 15.
Figure 16B:
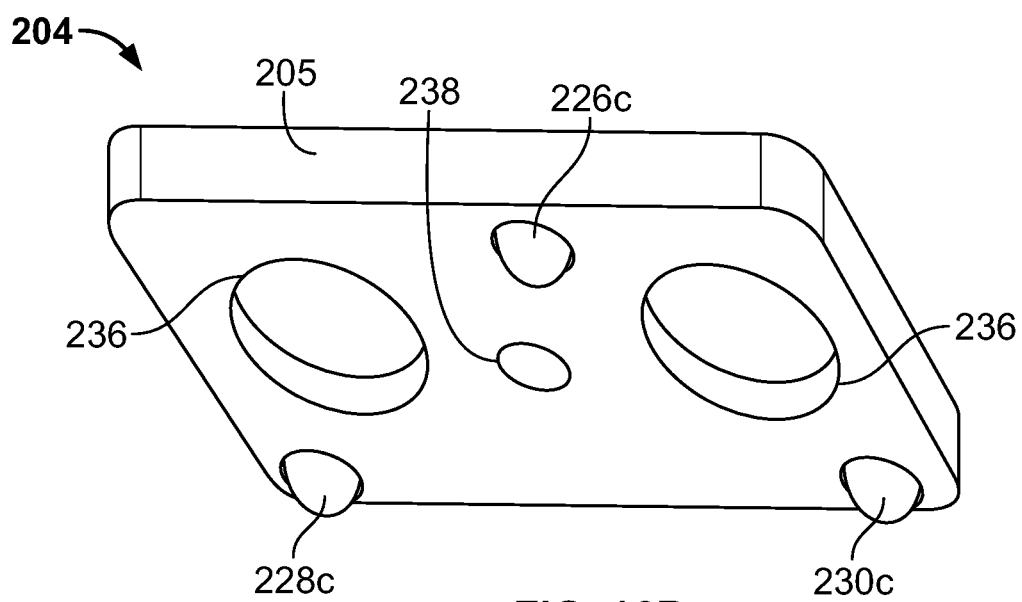
FIG. 16b is a bottom perspective view of a first plate of the collision protection switch of FIG. 15.
Figure 21A:
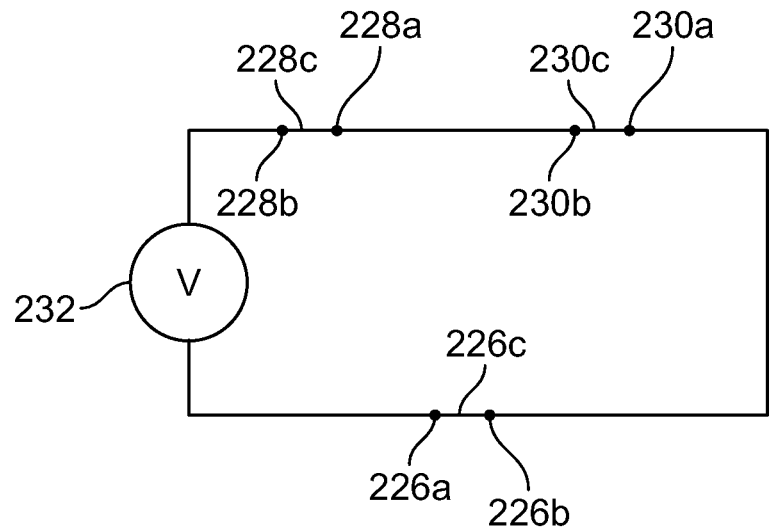
FIG. 21a is an electrical diagram of the collision protection switch of FIG. 15 in a closed position.
Figure 21B:
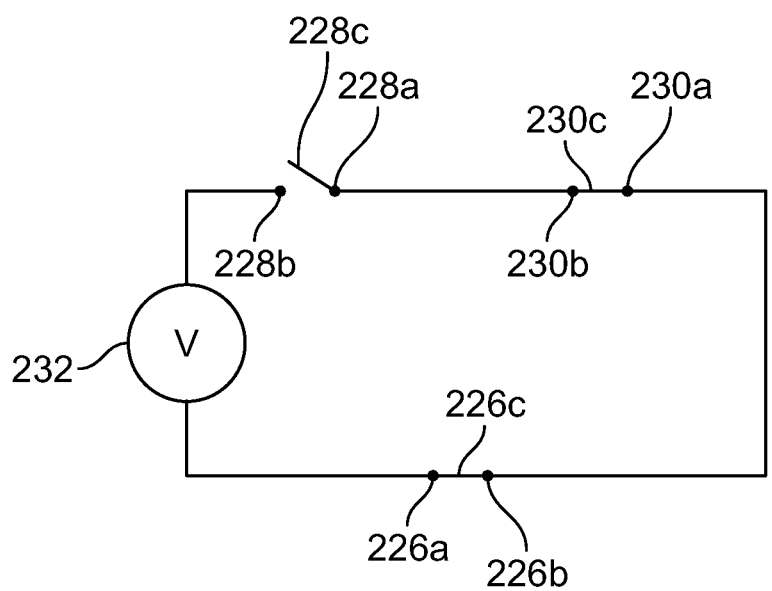
FIG. 21b is an electrical diagram of the collision protection switch of FIG. 15 in an open "collided" position.

As shown in FIG. 16b, the second plate 204 includes a housing 205 and three electrically conductive balls 226c, 228c, 230c secured to and extending from a bottom surface of the housing 205. The second plate housing 205 is substantially similar in geometry to the first plate housing 206, such that the location of the three electrically conductive balls 226c, 228c, 230c is aligned with the three circular bores 220, 222, 224 of the pin pockets 208, 210, 212. Further, the three balls 226c, 228c, 230c are arranged such that the center of each ball 226c, 228c, 230c is equidistant to each respective pin 226a, 226b, 228a, 228b, 230a, 230b of the pair of pains 226, 228, 230 that the ball 226c, 228c, 230c is matched with. The second plate housing 206 further includes two objective holes 236 extending therethrough that are aligned with the two threaded objective holes 216 of the first plate housing 206. Additionally, the second plate housing 206 includes a spring hole 238.

FIG. 17 shows a side view of the first plate 202 and the second plate 204 engaged and attached by an extension spring 231 that extends, and is secured between, the spring hole 218 of the first plate 202 and the spring hole 238 of the second plate 204. The spring 231 serves to pull the two plates together, nesting each of the balls 226c, 228c, 230c between the respective pair of pins 226, 228, 230, providing an arrangement of six normally-closed switches. In this "normally-engaged" mode, the series circuit formed between the voltage source 232 and the pins 226a, 226b, 228a, 228b, 230a, 230b of the first plate 202 is closed, such that electricity is flowing to the first pin 226a of the first pair of pins 226, the first and second pins 228a, 228b of the second pair of pins 228, and the second pin 230b of the third pair of pins 230 (as shown in the circuit diagram of FIG. 21a). However, as shown in FIG. 18, which shows a side view of the first plate 202 and the second plate 204 disengaged, when a source of force F on one of the objectives is enough to overcome the spring 231 connection force and cause one ball to move away from one of its two pin contacts, the circuit is opened and a collision "alarm" is triggered (as shown in the circuit diagram of FIG. 21b).

The collision protection switch 200 provides many options for alerting a user to the fact that the first plate 202 and the second plate are being forced apart, e.g., a collision event. For example, a light or alarm may be wired between the first pin 228a of the second pair of pins 228 and the second pin 230b of the third pair of pins 230 As such, when any one of the three electrically conductive balls 226c, 228c, 230c disengages any one pin 226, 228, 230, the circuit is opened and the light will illuminate or the alarm will sound. Alternatively, the circuit may be directly connected to a controller so that when one of the three electrically conductive balls 226c, 228c, 230c disengages a pin, the controller can immediately stop an associated motor, or may reverse the motor, thus preventing damage to a system that it may be connected to.

As shown in FIGS. 19 and 20, the first plate 202 and the second plate 204 can be fitted to a microscope, e.g., the microscope of a material test machine such as a microhardness tester, such that the microscope objective(s) extends between the two objective holes 236 of the second plate 204 and the two objective holes 216 of the first plate 202. In such an application, a user may bring the microscope objectives close to a sample for inspection, and accidentally contact the sample with the microscope objective. When this happens, damage may occur to not only the objective and the tester, but also the test specimen, which may be a valuable piece. However, with the collision protection switch 200 installed, when the user contacts the sample with the objective, a force F will be imparted on the objective and thus the second plate 202 causing the circuit to be opened, alerting the user to the collision. Alternatively, the motor driving the objectives toward the sample would be stopped or reversed upon opening of the circuit. After this alert, and subsequent re-engagement of the first plate 202 and the second plate 204, the microscope objectives re-seat to within a few microns as a result of the exactly-constrained configuration of the three pairs of pins 226, 228, 230 and three balls 226c, 228c, 230c. This configuration, with six contact points is exactly constrained. The two plates 202, 204 have only one settled position. When the plates 202, 204 are disturbed from that position (e.g. when a collision occurs), the plates 202, 204 will always return to exactly the same position and the microscope will be viewing the same position after the collision is cleared.

It should be understood by one of ordinary skill in the art that the first, second, and third pairs of parallel pins 226, 228, 230 may be arranged in any suitable positioning that will have six contact points and be exactly constrained. For example, the first, second, and third pairs of parallel pins 226, 228, 230 may be arranged so that each respective longitudinal axis intersect at approximately the center of the second plate 204.

Figure 22:
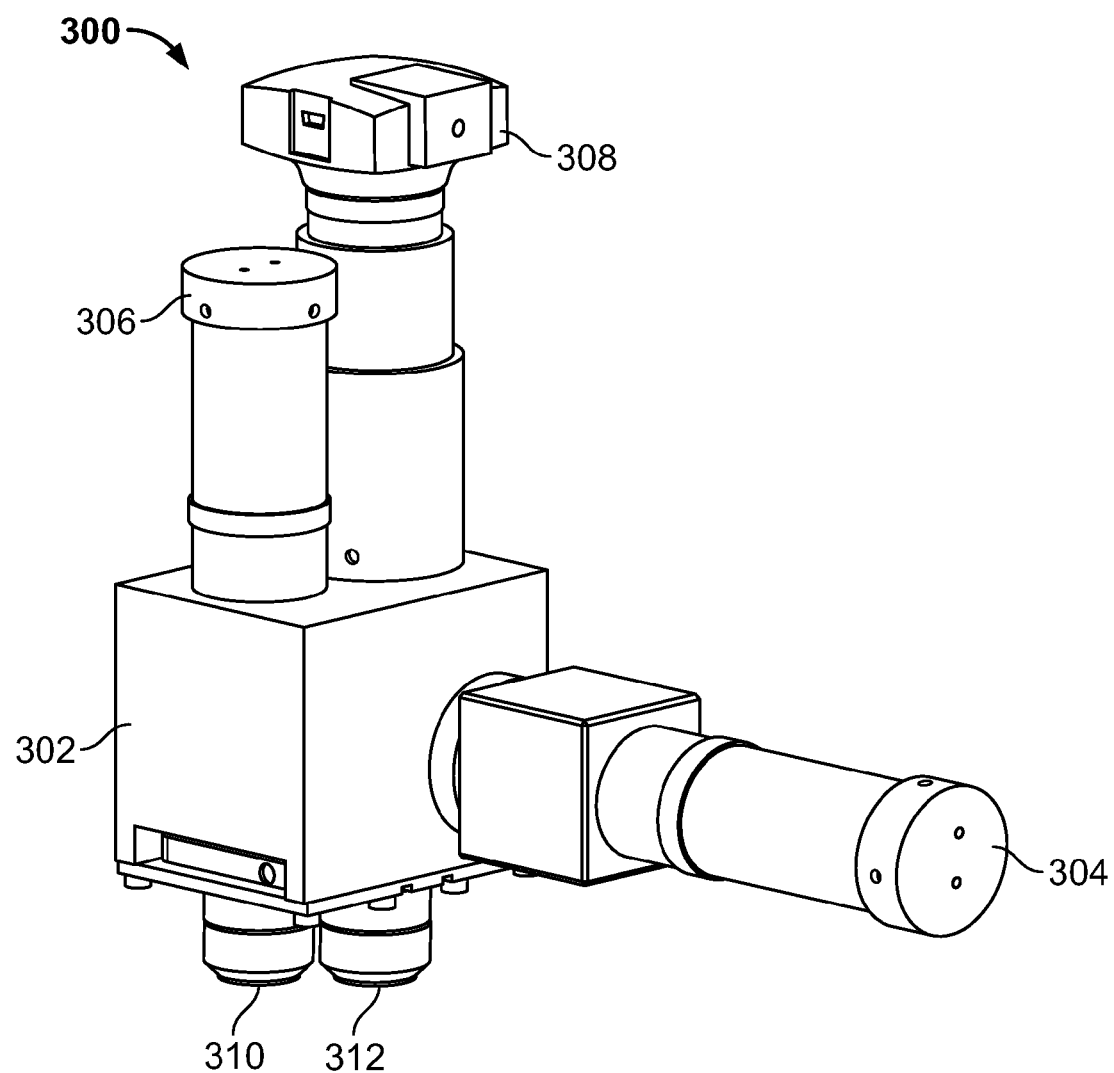
FIG. 22 is a perspective view of a two-objective microscope of the present invention.
Figure 23:
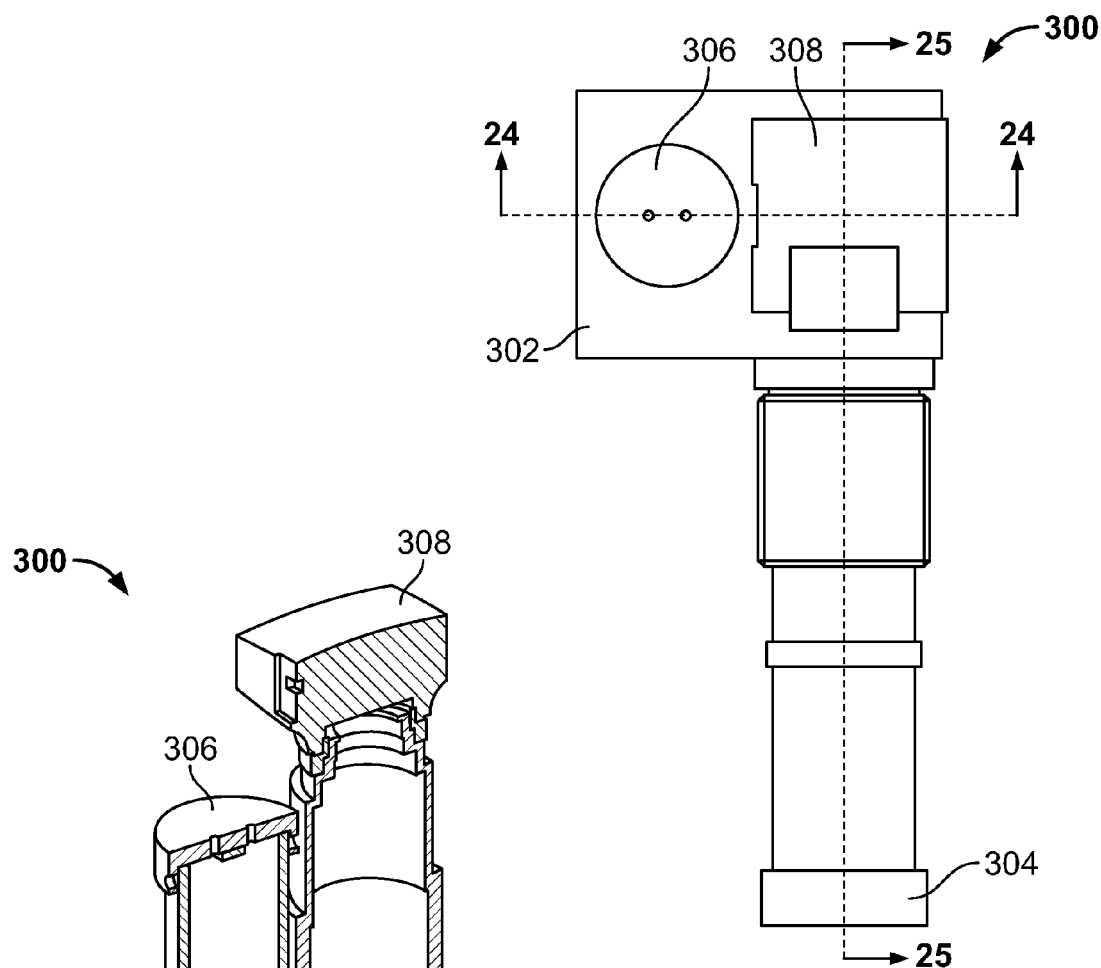
FIG. 23 is a top view of the two-objective microscope of FIG. 22.
Figure 24:
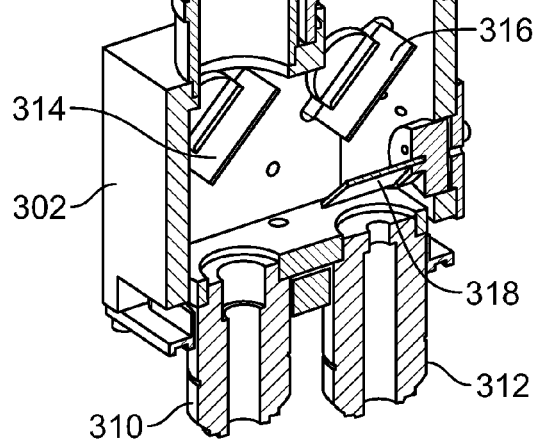
FIG. 24 is a partial sectional perspective view of the two-objective microscope of FIG. 22 taken along line 24-24 of FIG. 23.
Figure 25:
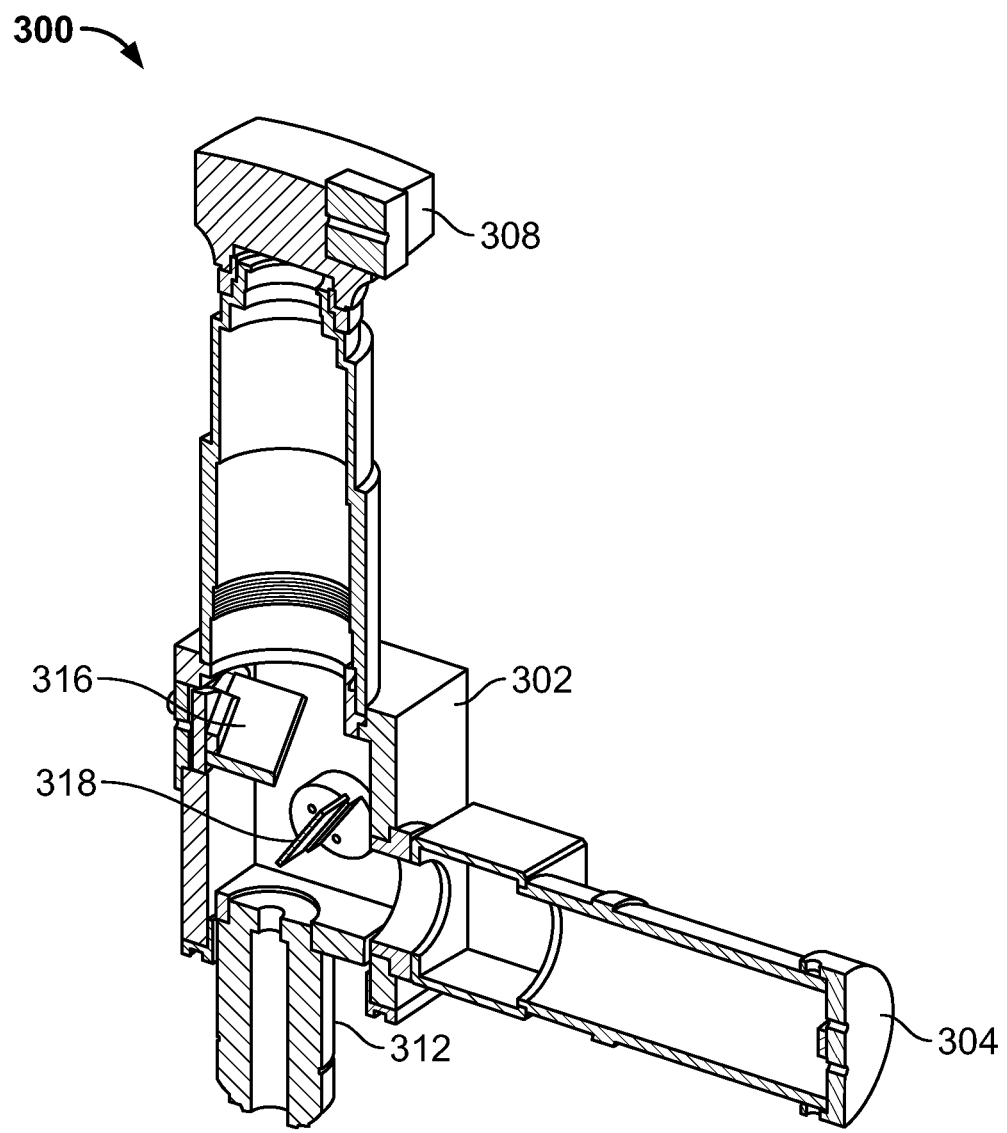
FIG. 25 is a partial sectional perspective view of the two-objective microscope of FIG. 22 taken along line 25-25 of FIG. 23.

FIGS. 22-25 illustrate a two-objective microscope of the present invention. FIG. 22 is a perspective view of the two-objective microscope 300 showing a housing 302, a lower light emitting diode (LED) 304, an upper LED 306, a camera 308, and two in-line objectives 310, 312. FIG. 23 is a top view of the two-objective microscope 300. FIGS. 24 and 25 are partial sectional views of the two-objective microscope 300 showing the components of the housing 302. The housing 302 includes a first half-mirror 314, a second half-mirror 316, and a third half-mirror 318.

The components of the two-objective microscope 300 are arranged such that the camera 308, the second half-mirror 316, and the third half-mirror 318, and the second objective 312 are in-line, while the upper LED 306, the first half-mirror 314, and the first objective 310 are in-line. As shown in FIG. 24, in an example embodiment, the first half-mirror 314 and the second half-mirror 316 are positioned parallel to each other and on the same horizontal axis, but rotated such that a light returned through the first objective 310 will reflect off the first half-mirror 314 to the second half-mirror 316 and up through the tube lens and into the camera 308. The mirrors are each rotated 45° clock-wise from the viewing angle. As shown in FIG. 25, the third half-mirror 318 is positioned to reflect light from the lower LED 304 down into the objective 312. The light reflected from the sample travels vertically up, through the second objective 312, through each half-mirror 316, 318 and up through the tube lens and into the camera 308.

The half-mirrors 314, 316, and 318 reflect ½ of the light that is shone on the mirror and permit the remaining ½ of the light that is shone on the mirror to pass through. As such, and because of the arrangement described above, when a user wishes to view a specimen through the first objective 310, he/she would illuminate the upper LED 306. When the upper LED 306 is illuminated, the light will shine on the first half-mirror 314 that will reflect ½ of the light that will be lost and permit ½ of the light to pass through to the first objective 310. The ½ of the light will then pass through the first objective 310, reflect off a specimen and back through the first objective 310, and engage the first half-mirror 314 again. During this engagement, ½ of the light, e.g., ¼ of the original light, will pass through the first half-mirror 314 towards the upper LED 306 and will be lost, while the next ½ of the light, e.g., ¼ of the original light, will reflect off the first half-mirror 314 at a 90° angle towards the second half-mirror 316. This ¼ of the light will engage the second half-mirror 316 and ½, e.g., ⅛ of the original light, will pass through and be lost, while the next ½, e.g., ⅛ of the original light, will be reflected to the camera 308. Thus, the camera 308 ultimately receives an image of the specimen at ⅛ the original LED light strength. Alternatively, when a user wishes to view a specimen through the second objective 312, he/she would illuminate the lower LED 304, which is positioned perpendicular to the second objective 312 and in-line with the third half-mirror 318. When the lower LED 304 is illuminated, the light will shine on the third half-mirror 318 that will permit ½ of the light to pass through, which will be lost, and reflect the other ½ of the light toward the second objective 312. The ½ of the light will then pass through the second objective 312, reflect off a specimen and back through the second objective 312, and engage the third half-mirror 318 again. During this engagement, ½ of the light, e.g., ¼ of the original light, will reflect off the third half-mirror 314 towards the lower LED 304 and will be lost, while the next ½ of the light, e.g., ¼ of the original light, will pass through the third half-mirror 314 towards the second half-mirror 316. This ¼ of the light will engage the second half-mirror 316 and ½, e.g., ⅛ of the original light, will reflect away and be lost, while the next ½, e.g., ⅛ of the original light, will pass through to the camera 308. Thus, the camera 308 ultimately receives an image of the specimen at ⅛ the original LED light strength.

As such, when a user wishes to change the camera view from the first objective 310 to the second objective 312, all that has to be done is the switching of the light source 304, 306. The two-objective microscope 300 can be connected to a computer so that images of the specimen are transmitted digitally thereto and shown on a computer screen.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. An adjustable stage mount, comprising:
   a housing including a base defining a hole and an annular protrusion extending from the base;
   an adjustable stage including a mounting surface and a ball joint extension extending from the mounting surface and defined by a ball joint extension wall and a semi-spherical end, the wall including at least one radial bore extending therethrough;
   the annular protrusion including a central axis and further including a plurality of xy-axis bores extending therethrough in a sloped radial configuration and a z-axis locking assembly, the z-axis locking assembly including a radial pin hole, oriented radially with respect to the annular protrusion, and two z-axis bores perpendicular to the radial pin hole, and offset from the central axis of the annular protrusion;
   a pin configured to engage the at least one radial bore;
   a plurality of xy-axis bolts configured to engage the plurality of xy-axis bores and to contact the ball joint extension wall; and
   a plurality of z-axis bolts configured to engage the two z-axis bores and to contact the pin, wherein the semi-spherical end is configured to rotatably engage the hole.

2. The adjustable stage mount of claim 1, wherein the adjustable stage includes a mounting plate.

3. The adjustable stage mount of claim 2, wherein the mounting plate includes a plurality of bores configured to mount a component.

4. The adjustable stage mount of claim 1, wherein the housing includes a plurality of mounting slots configured to removably mount the housing.

5. The adjustable stage mount of claim 1, wherein the housing includes one or more T-shaped protrusions extending from a bottom of the base.

6. The adjustable stage mount of claim 1, wherein the hole is defined by a rounded edge.

7. The adjustable stage mount of claim 1, wherein the ball joint extension wall includes a plurality of radial bores.

8. The adjustable stage mount of claim 1, wherein the ball joint extension wall is configured as a conical wall.

9. The adjustable stage mount of claim 1, wherein the xy-bores extend through the annular protrusion at an angle.

10. An adjustable indenter mount, comprising:
a housing including a shoulder defining a hole and an annular protrusion;
an adjustable indenter including an indenter tip mount and a ball joint extension extending from the indenter tip mount and defined by a ball joint extension wall and a semi-spherical end, the wall including at least one radial bore extending therethrough;
the annular protrusion including a central axis and further including a plurality of xy-axis bores extending therethrough in a sloped radial configuration and a z-axis locking assembly, the z-axis locking assembly including a radial pin hole, oriented radially with respect to the annular protrusion, and two z-axis bores perpendicular to the radial pin hole, and offset from the central axis of the annular protrusion;
a pin configured to engage that at lest one radial bore;
a plurality of xy-axis bolts configured to engage the plurality of xy-axis bores and to contact the ball joint extension wall; and
a plurality of z-axis bolts configured to engage the two z-axis bores and to contact the pin, wherein the semi-spherical end is configured to rotatably engage the hole.

11. The adjustable indenter mount of claim 10, further comprising:
an indenter tip; and
a collar adapted to removably attach to the indenter tip mount,
wherein the collar is configured to secure the indenter tip to the indenter tip mount.

12. The adjustable indenter mount of claim 11, wherein the collar is adapted to removably connect to the indenter tip mount with a snap-fit connection.

13. The adjustable indenter mount of claim 11, wherein the indenter tip mount includes external threading and the collar includes internal threading for mating with the external threading of the indenter tip mount.

14. The adjustable indenter mount of claim 10, wherein the housing is configured to be attached to an indenter machine.

15. The adjustable indenter mount of claim 10, wherein the shoulder includes a rounded edge defining the hole.

16. The adjustable indenter mount of claim 10, wherein the ball joint extension wall includes a plurality of radial bores.

17. The adjustable indenter mount of claim 10, wherein the ball joint extension wail is configured as a conical wall.

18. The adjustable indenter mount of claim 10, wherein the xy-bores extend through the annular protrusion at an angle.

19. A microhardness tester, comprising:
the adjustable stage mount of claim 1; and
a collision protection switch, comprising:
a first plate formed of an electrically insulative material, the first plate including a first, a second, and a third pair of electrically conductive pins;
the first pair, the second pair, and the third pair of electrically conductive pins each including a first pin and a second pin spaced apart from each other, the first pin of the first pair of electrically conductive pins in electrical communication with the second pin of the second pair of electrically conductive pins, and the first pin of the second pair of electrically conductive pins in electrical communication with the second pin of the third pair of electrically conductive pins;
a voltage source in electrical communication with the first pin of the third pair of electrically conductive pins and the second pin of the first pair of electrically conductive pins;
a second plate formed of an electrically insulative material, the second plate including a first electrically conductive ball, a second electrically conductive ball, and a third electrically conductive ball extending from a wall thereof; and
a retention spring forcing the first plate and the second plate together in a first position where the first electrically conductive ball engages the first pair of electrically conductive pins, the second electrically conductive ball engages the second pair of electrically conductive pins, and the third electrically conductive ball engages the third pair of electrically conductive pins, forming a closed circuit,
wherein the first electrically conductive ball, the second electrically conductive ball, and the third electrically conductive ball are configured such that if any one disengages the respective first pair, second pair, or third pair of electrically conductive pins the circuit is opened.

20. The microhardness tester of claim 19, wherein the first plate further comprises:
a first internal pocket housing the first pair of electrically conductive pins and accessible by a first aperture in the first plate;
a second internal pocket housing the second pair of electrically conductive pins and accessible by a second aperture in the first plate; and
a third internal pocket housing the third pair of electrically conductive pins and accessible by a third aperture in the first plate.

21. The microhardness tester of claim 19, further comprising a light in electrical communication with the circuit,
wherein the light is configured to deluminate when the circuit is opened.

22. The microhardness tester of claim 19, further comprising an alarm in electrical communication with the circuit,
wherein the alarm is configured to sound when the circuit is opened.

23. The microhardness tester of claim 19, further comprising a controller in electrical communication with the circuit,
wherein the controller is configured to turn off a motor associated with the controller when the circuit is opened.

24. The microhardness tester of claim 19, further comprising at least one microscope objective in mechanical communication with at least one of the first plate and the second plate such that a force against the at least one microscope objective forces the first plate and the second plate away from each other to open the circuit.

25. A microhardness tester, comprising:
   the adjustable stage mount of claim 1; and
   a two-objective microscope, comprising:
      a first objective parallel with a second objective;
      an upper light source configured to provide light to the first objective;
      a lower light source configured to provide light to the second objective;
      a first half-mirror;
      a second half-mirror;
      a third half-mirror; and
      a camera configured to view through the first objective and the second objective,
      wherein the camera views through the first objective when the upper light source is switched on and through the second objective when the lower light source is switched on.

26. The microhardness tester of claim 25, wherein the first light source and the second light source are light emitting diodes.

* * * * *